(12) United States Patent
Sengun et al.

(10) Patent No.: US 10,821,005 B2
(45) Date of Patent: **\*Nov. 3, 2020**

(54) METHODS AND DEVICES FOR DELIVERING AND AFFIXING TISSUE SCAFFOLDS

(71) Applicant: DePuy Synthes Products, Inc., Raynham, MA (US)

(72) Inventors: Mehmet Z. Sengun, Canton, MA (US); Kristian DiMatteo, Waltham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 247 days.

This patent is subject to a terminal disclaimer.

(21) Appl. No.: 15/832,908

(22) Filed: Dec. 6, 2017

(65) Prior Publication Data
US 2018/0092759 A1    Apr. 5, 2018

Related U.S. Application Data

(60) Continuation of application No. 14/828,854, filed on Aug. 18, 2015, now Pat. No. 9,848,999, which is a
(Continued)

(51) Int. Cl.
*A61F 2/46* (2006.01)
*A61F 2/30* (2006.01)

(52) U.S. Cl.
CPC .. *A61F 2/4618* (2013.01); *A61F 2002/30766* (2013.01); *A61F 2002/4627* (2013.01)

(58) Field of Classification Search
CPC ............. A61B 17/1604; A61B 17/1635; A61F 2/30767; A61F 2/46; A61F 2/4601;
(Continued)

(56) References Cited

U.S. PATENT DOCUMENTS

| 4,026,030 A | 5/1977 | Kuever et al. |
| 4,945,904 A | 8/1990 | Bolton et al. |

(Continued)

FOREIGN PATENT DOCUMENTS

| CA | 2101266 A1 | 7/1992 |
| CN | 1913844 A | 2/2007 |

(Continued)

OTHER PUBLICATIONS

Indian Examination Report in IN App. No. 350/KOL/2010 dated Dec. 24, 2018 (4 pages).
Indian Examination Report for IN App. No. 349/KOL/2010 dated Oct. 29, 2018 (6 pages).
(Continued)

*Primary Examiner* — Ryan J. Severson

(57) ABSTRACT

Methods and devices are provided for delivering and affixing tissue replacements. In one embodiment, a tissue scaffold can be delivered into a patient through a cannula to a cavity formed at a defect site in tissue, e.g., cartilage. A delivery shaft can be used to deliver the scaffold through the cannula, and a loading device can help load the scaffold onto the delivery shaft. A delivery guide device can position and temporarily hold the scaffold within the cavity. The delivery guide device can guide one or more surgical instruments to the scaffold to affix the scaffold within the cavity, e.g., to bone underlying the scaffold, using at least one securing mechanism.

19 Claims, 10 Drawing Sheets

Related U.S. Application Data division of application No. 13/542,004, filed on Jul. 5, 2012, now Pat. No. 9,149,369, which is a continuation of application No. 12/412,499, filed on Mar. 27, 2009, now Pat. No. 8,241,298.

(58) Field of Classification Search
CPC ............ A61F 2/4618; A61F 2002/4625; A61F 2002/4627; A61F 2002/4687
See application file for complete search history.

(56) References Cited

U.S. PATENT DOCUMENTS

| | | | |
|---|---|---|---|
| 5,306,311 A | 4/1994 | Stone et al. | |
| 5,484,403 A | 1/1996 | Yoakum et al. | |
| 5,632,745 A | 5/1997 | Schwartz | |
| 5,676,146 A | 10/1997 | Scarborough | |
| 5,690,674 A | 11/1997 | Diaz | |
| 5,769,899 A | 6/1998 | Schwartz et al. | |
| 5,876,440 A | 3/1999 | Feingold | |
| 5,885,293 A | 3/1999 | McDevitt | |
| 6,001,107 A | 12/1999 | Feingold | |
| 6,080,194 A | 6/2000 | Pachence et al. | |
| 6,143,000 A | 11/2000 | Feingold | |
| 6,176,880 B1 | 1/2001 | Plouhar et al. | |
| 6,179,840 B1 | 1/2001 | Bowman | |
| 6,251,132 B1 | 6/2001 | Ravenscroft et al. | |
| 6,251,143 B1 | 6/2001 | Schwartz et al. | |
| 6,356,782 B1 | 3/2002 | Sirimanne et al. | |
| 6,358,253 B1 | 3/2002 | Torrie et al. | |
| 6,364,884 B1 | 4/2002 | Bowman et al. | |
| 6,402,766 B2 | 6/2002 | Bowman et al. | |
| 6,423,073 B2 | 7/2002 | Bowman | |
| 6,436,068 B1 | 8/2002 | Bardy | |
| 6,436,110 B2 | 8/2002 | Bowman et al. | |
| 6,447,517 B1 | 9/2002 | Bowman | |
| 6,468,314 B2 | 10/2002 | Schwartz et al. | |
| 6,497,707 B1 | 12/2002 | Bowman et al. | |
| 6,610,067 B2 | 8/2003 | Tallarida et al. | |
| 6,669,706 B2 | 12/2003 | Schmitt et al. | |
| D491,807 S | 6/2004 | Cauldwell et al. | |
| D494,063 S | 8/2004 | Cauldwell et al. | |
| 6,852,125 B2 | 2/2005 | Simon et al. | |
| 6,852,330 B2 | 2/2005 | Bowman et al. | |
| 6,858,042 B2 | 2/2005 | Nadler et al. | |
| 6,884,428 B2 | 4/2005 | Binette et al. | |
| 6,979,330 B2 | 12/2005 | Kelly et al. | |
| 7,115,100 B2 | 10/2006 | McRury et al. | |
| 7,160,326 B2 | 1/2007 | Ball | |
| 7,163,563 B2 | 1/2007 | Schwartz et al. | |
| 7,166,133 B2* | 1/2007 | Evans .................... | A61L 27/12 623/23.51 |
| 7,214,232 B2* | 5/2007 | Bowman ............ | A61B 17/0401 606/232 |
| 7,235,107 B2 | 6/2007 | Evans et al. | |
| 7,476,250 B1 | 1/2009 | Mansmann | |
| 7,571,729 B2 | 8/2009 | Saadat et al. | |
| 7,794,408 B2 | 9/2010 | Binette et al. | |
| 7,819,880 B2* | 10/2010 | Zannis ................. | A61F 2/4618 606/86 A |
| 8,241,298 B2 | 8/2012 | Sengun et al. | |
| 8,308,814 B2 | 11/2012 | Sengun et al. | |
| 8,469,980 B2 | 2/2013 | Sengun et al. | |
| 8,673,021 B2* | 3/2014 | Orr ................. | A61B 17/00234 623/23.72 |
| 9,149,369 B2 | 10/2015 | Sengun et al. | |
| 9,421,082 B2 | 8/2016 | Sengun et al. | |
| 9,848,999 B2 | 12/2017 | Sengun et al. | |
| 2001/0010023 A1 | 7/2001 | Schwartz et al. | |
| 2002/0052628 A1 | 5/2002 | Bowman | |
| 2002/0095157 A1 | 7/2002 | Bowman | |
| 2002/0119177 A1 | 8/2002 | Bowman et al. | |
| 2002/0127265 A1 | 9/2002 | Bowman et al. | |
| 2002/0147498 A1 | 10/2002 | Tallarida et al. | |
| 2002/0169465 A1 | 11/2002 | Bowman et al. | |
| 2003/0033022 A1 | 2/2003 | Plouhar et al. | |
| 2003/0036801 A1 | 2/2003 | Schwartz et al. | |
| 2003/0055502 A1 | 3/2003 | Lang et al. | |
| 2003/0147935 A1 | 8/2003 | Binette et al. | |
| 2003/0216669 A1 | 11/2003 | Lang et al. | |
| 2003/0236573 A1 | 12/2003 | Evans et al. | |
| 2004/0015170 A1 | 1/2004 | Tallarida et al. | |
| 2004/0059425 A1 | 3/2004 | Schmieding | |
| 2004/0078077 A1 | 4/2004 | Binette et al. | |
| 2004/0078090 A1 | 4/2004 | Binette et al. | |
| 2004/0138664 A1 | 7/2004 | Bowman | |
| 2004/0147927 A1 | 7/2004 | Tsougarakis et al. | |
| 2004/0175408 A1 | 9/2004 | Chun et al. | |
| 2004/0193071 A1 | 9/2004 | Binette et al. | |
| 2004/0193154 A1 | 9/2004 | Leatherbury et al. | |
| 2004/0267277 A1 | 12/2004 | Zannis et al. | |
| 2004/0267362 A1 | 12/2004 | Hwang et al. | |
| 2005/0038520 A1 | 2/2005 | Binette et al. | |
| 2005/0054595 A1 | 3/2005 | Binette et al. | |
| 2005/0059862 A1 | 3/2005 | Phan | |
| 2005/0059905 A1 | 3/2005 | Boock et al. | |
| 2005/0113736 A1 | 5/2005 | Orr et al. | |
| 2005/0113937 A1 | 5/2005 | Binette et al. | |
| 2005/0113938 A1 | 5/2005 | Jamiolkowski et al. | |
| 2005/0125077 A1 | 6/2005 | Harmon et al. | |
| 2005/0137600 A1 | 6/2005 | Jacobs et al. | |
| 2005/0154399 A1 | 7/2005 | Weber et al. | |
| 2005/0177249 A1 | 8/2005 | Kladakis et al. | |
| 2005/0209610 A1 | 9/2005 | Carrison | |
| 2005/0222687 A1 | 10/2005 | Vunjak-Novakovic et al. | |
| 2005/0232967 A1 | 10/2005 | Kladakis et al. | |
| 2005/0234549 A1 | 10/2005 | Kladakis et al. | |
| 2006/0009798 A1 | 1/2006 | Callister et al. | |
| 2006/0060209 A1 | 3/2006 | Shepard | |
| 2006/0173539 A1 | 8/2006 | Shiuey | |
| 2006/0178748 A1 | 8/2006 | Dinger et al. | |
| 2006/0224242 A1 | 10/2006 | Swords et al. | |
| 2006/0241568 A1 | 10/2006 | Roger | |
| 2006/0241756 A1 | 10/2006 | Fritz et al. | |
| 2006/0247790 A1 | 11/2006 | McKay | |
| 2006/0257379 A1 | 11/2006 | Giordano et al. | |
| 2006/0292131 A1 | 12/2006 | Binette et al. | |
| 2006/0293760 A1 | 12/2006 | DeDeyne | |
| 2007/0031470 A1 | 2/2007 | Kladakis et al. | |
| 2007/0038299 A1 | 2/2007 | Stone et al. | |
| 2007/0043376 A1 | 2/2007 | Leatherbury et al. | |
| 2007/0073394 A1 | 3/2007 | Seedhom et al. | |
| 2007/0100462 A1 | 5/2007 | Lang et al. | |
| 2007/0106306 A1 | 5/2007 | Bodduluri et al. | |
| 2007/0123915 A1 | 5/2007 | Kammerer et al. | |
| 2007/0148242 A1 | 6/2007 | Vilei et al. | |
| 2007/0198022 A1 | 8/2007 | Lang et al. | |
| 2007/0233135 A1 | 10/2007 | Gil et al. | |
| 2008/0167729 A1 | 7/2008 | Nelson et al. | |
| 2008/0181954 A1 | 7/2008 | Binette et al. | |
| 2008/0208198 A1 | 8/2008 | Nycz et al. | |
| 2008/0208347 A1 | 8/2008 | Muratoglu et al. | |
| 2008/0234715 A1 | 9/2008 | Pesce et al. | |
| 2008/0243127 A1 | 10/2008 | Lang et al. | |
| 2008/0304725 A1 | 12/2008 | Leitner | |
| 2009/0275966 A1 | 11/2009 | Mitusina | |
| 2010/0249758 A1 | 9/2010 | Sengun et al. | |
| 2010/0249801 A1 | 9/2010 | Sengun et al. | |
| 2012/0271432 A1 | 10/2012 | Sengun et al. | |
| 2013/0041380 A1 | 2/2013 | Sengun et al. | |
| 2013/0197666 A1 | 8/2013 | Sengun et al. | |
| 2015/0351931 A1* | 12/2015 | Sengun ................. | A61F 2/4618 623/23.72 |
| 2016/0361172 A1 | 12/2016 | Sengun et al. | |
| 2018/0092759 A1* | 4/2018 | Sengun ................. | A61F 2/4618 |

FOREIGN PATENT DOCUMENTS

| | | |
|---|---|---|
| DE | 3637081 C1 | 2/1988 |
| EP | 1070487 A2 | 1/2001 |
| GB | 2452987 A | 3/2009 |
| JP | 01-171693 U | 12/1989 |
| JP | H07507091 A | 8/1995 |
| WO | WO-0139694 A2 | 6/2001 |

(56) References Cited

FOREIGN PATENT DOCUMENTS

| WO | WO-03/028535 | 4/2003 |
|----|--------------|--------|
| WO | WO-03051210 A2 | 6/2003 |
| WO | WO-05051245 A2 | 6/2005 |

OTHER PUBLICATIONS

Chinese Search Report in CN Application No. 201410482528.7 dated Jan. 12, 2016 (English translation).
European Examination Report in EP App. No. 10250621.9 dated Jan. 30, 2017.
European Search Report and Written Opinion in EP App. No. 11173980.1 dated Sep. 12, 2011 (6 pages).
Extended European Search Report in EP App. No. 10250619.3 dated Dec. 21, 2010 (12 pages).
Japanese Office Action for Application No. 2014-177845 dated Jun. 30, 2015. (English translation only).
Office Action in U.S. Appl. No. 12/412,492 dated Apr. 4, 2012.
Office Action in U.S. Appl. No. 12/412,492 dated Jun. 21, 2011.
Office Action in U.S. Appl. No. 12/412,492 dated Nov. 16, 2011.
Office Action in U.S. Appl. No. 12/412,499 dated Dec. 23, 2011.
Office action issued in Japanese Application No. 2010071684 dated Jan. 7, 2014. (English translation only).
Office action issued in Japanese Application No. 2010071692 dated Jan. 7, 2014. (English translation only).
Partial European Search Report in EP App. No. 10250619.3 dated Jul. 5, 2010 (5 pages).
Partial European Search Report issued in European Application No. 10250621.9 dated Jul. 3, 2014.
European Search Report and Written Opinion in EP App. No. 17203054.6 dated May 30, 2018 (9 pages).

* cited by examiner

METHODS AND DEVICES FOR DELIVERING AND AFFIXING TISSUE SCAFFOLDS

CROSS-REFERENCE TO RELATED APPLICATIONS

This application is a continuation of U.S. patent application Ser. No. 14/828,854, filed on Aug. 18, 2015, and entitled "Methods and Devices for Delivering and Affixing Tissue Scaffolds," which is a divisional of U.S. patent application Ser. No. 13/542,004, filed on Jul. 5, 2012, and entitled "Methods and Devices for Delivering and Affixing Tissue Scaffolds," which is a continuation of U.S. patent application Ser. No. 12/412,499 (now U.S. Pat. No. 8,241,298), filed on Mar. 27, 2009, and entitled "Methods and Devices for Delivering and Affixing Tissue Scaffolds," which are incorporated herein by reference in their entireties.

FIELD OF THE INVENTION

The present invention relates to methods and devices for delivering and affixing tissue scaffolds.

BACKGROUND OF THE INVENTION

Injuries to soft tissue, such as cartilage, skin, muscle, bone, tendon, and ligament, frequently require surgical intervention to repair the damage and facilitate healing. Such surgical repairs can include suturing or otherwise repairing the damaged tissue with known medical devices, augmenting the damaged tissue with other tissue, using an implant, a graft, or any combination of these techniques.

One common tissue injury involves damage to cartilage, which is a non-vascular, resilient, flexible connective tissue. Cartilage typically acts as a "shock-absorber" at articulating joints, but some types of cartilage provide support to tubular structures, such as for example, the larynx, air passages, and the ears. In general, cartilage tissue is comprised of cartilage cells, known as chondrocytes, located in an extracellular matrix, which contains collagen, a structural scaffold, and aggrecan, a space-filling proteoglycan. Several types of cartilage can be found in the body, including hyaline cartilage, fibrocartilage, and elastic cartilage. Hyaline cartilage can appear in the body as distinct pieces, or alternatively, this type of cartilage can be found fused to the articular ends of bones. Hyaline cartilage is generally found in the body as articular cartilage, costal cartilage, and temporary cartilage (i.e., cartilage that is ultimately converted to bone through the process of ossification). Fibrocartilage is a transitional tissue that is typically located between tendon and bone, bone and bone, and/or hyaline cartilage and hyaline cartilage. Elastic cartilage, which contains elastic fibers distributed throughout the extracellular matrix, is typically found in the epiglottis, the ears, and the nose.

One common example of hyaline cartilage injury is a focal articular cartilage defect in the knee. A strong impact to the joint can result in the partial removal of a cartilage fragment of various size and shape or sufficiently damage the extracellular matrix of the cartilage to cause degeneration of cartilage. If left untreated, damaged articular cartilage can restrict joint function, cause debilitating pain and may result in long term chronic diseases such as osteoarthritis, a disease characterized by cartilage breakdown and unfavorable changes in the underlying bone. As injuries to the articular cartilage tissue generally do not heal on their own, surgical intervention is often necessary to repair symptomatic lesions. The current modality of treatment consists of lavage, removal of partially or completely unattached tissue fragments. In addition, the surgeon will often use a variety of methods such as abrasion, drilling, or microfractures, to induce bleeding into the cartilage defect and formation of a clot. It is believed that the cells coming from the marrow will form a scar-like tissue that is fibrocartilaginous in nature and can only provide temporary relief to some symptoms. Unfortunately, the repair tissue does not have the same mechanical properties as hyaline cartilage and therefore degrades faster over time as a consequence of wear. Patients typically require a secondary procedure to alleviate symptoms.

More recently, experimental approaches involving the implantation of autologous chondrocytes have been used with increasing frequency. The chondrocytes are obtained by harvesting a piece of cartilage from a patient using a biopsy and then cells are extracted from the tissue sample and cultured to the appropriate numbers in the laboratory. The expanded chondrocytes are then provided to the surgeon in the form of a cell suspension or pre-loaded onto a synthetic or natural biodegradable, biocompatible scaffold for placement into the cartilage defect site. Sometimes, these living cells are placed in a three-dimensional natural or synthetic scaffold or matrix, and are kept under tissue specific culture conditions to create a transplantable function tissue replacement. If provided with the appropriate conditions and signals, the cells will proliferate, differentiate, and secrete various matrix molecules to create an actual living tissue that can be used as a replacement tissue to be implanted back into the defect site in the patient.

Other techniques for repairing damaged cartilage employ cells other than chondrocytes to produce the desired hyaline-like tissue. Stem or progenitor cells, such as the cells within fatty tissue, muscle, or bone marrow, have the potential to regenerate bone and/or cartilage in a patient. Stem cells can be from that patient, i.e., autogeneic, or from another patient, i.e., allogeneic. These progenitor cells in addition to other cells, such as cells from the synovium, are thought to regenerate cartilage tissue when placed in an environment favorable for inducing cartilage formation.

Other surgical techniques for the surgical treatment of damaged tissue include the use of surgical implants, scaffolds, or matrices. Various surgical implants have been used in surgical procedures to help regenerate cartilage without the use of cells. For example, implants can be created consisting of porous biodegradable, biocompatible polymeric matrices. Other examples include matrices derived from biopolymers such as hyaluronic acid, collagen, and fibrin. These implants are often used in conjunction with marrow stimulation techniques, such as microfracture, such that the marrow can provide the cells as well as other stimulants that will help to regenerate cartilage.

Before an implant can be placed into the patient, preparations must be made to both the defect site and the implant to ensure good integration of the implant with the cartilage surrounding the defect. The patient must be prepared by clearing the degenerate or damaged tissue from the defect site. Particularly in arthroscopic procedures where access to the surgical site is limited, clearing space at the defect site can be difficult and time consuming in attempts to minimize any trauma to the neighboring healthy cartilage and/or subchondral bone, i.e., the bone underlying the defect. The implant must also be prepared by sizing it from its laboratory-created size to match the cleared defect space in the patient. Because the implant cannot be appropriately sized until the space at the defect site in the patient has been formed and its size can be identified, the implant has to be prepared for implantation ad hoc during the surgical procedure. Errors in sizing the implant during the stress of surgery can prolong the surgical procedure and can result in repeated resizing of the tissue replacement to an acceptable size. In some cases attempts to size the implant can result in no appropriately sized implant if it has been cut to one or more unusable sizes. An unusable implant can necessitate creation of another implant in another expensive, time-consuming, and medically intrusive process followed by another attempt at implantation in the patient.

Accordingly, there remains a need for methods and devices for placing an implant into the patient.

SUMMARY OF THE INVENTION

The present invention generally provides methods and devices for delivering and affixing tissue scaffolds. In one embodiment, a tissue scaffold loading system is provided that includes a delivery shaft having at least one prong that extends from a distal end thereof and that is configured to extend through a tissue scaffold. The tissue scaffold loading system also includes a loading block having a surface configured to seat a tissue scaffold thereon, the surface having at least one opening formed therein and configured to receive the at least one prong on the delivery shaft such that the at least one prong can extend through a tissue scaffold seated on the surface. The loading block further includes a guide member extending from the surface and having at least one channel formed therein that is positioned to guide the at least one prong into the at least one opening on the surface.

The tissue scaffold loading system can have any number of variations. For example, the at least one prong can include two prongs, the at least one opening can include two openings, and the at least one channel can include two channels. The at least one opening formed in the surface of the loading block can be in the form of an elongate slot configured to allow the at least one prong on the elongate shaft to slide therein. For another example, the at least one opening can be located a predetermined distance from a terminal edge of the surface such that the at least one prong will extend through a predetermined location on a tissue scaffold seated on the surface and having perimeter abutting the terminal edge. In some embodiments, the guide member can have a first portion extending substantially perpendicular to the surface and a second portion extending substantially parallel to the surface, the at least one channel being formed in the second portion. The tissue scaffold loading system can include a tissue scaffold having a plurality of pores, each of the pores having a diameter substantially equal to a diameter of the at least one prong.

In some embodiments, the tissue scaffold loading system can include a delivery cannula having an inner lumen extending therethrough and configured to receive the delivery shaft therein. A funnel can be removably mated to a distal end of the delivery cannula. The delivery shaft can be configured to be inserted into a distal end of the delivery cannula, and the delivery cannula can include a stop configured to limit proximal movement of the delivery shaft within the delivery cannula to position the at least one prong at a predetermined location within the distal end of the delivery cannula. The tissue scaffold loading system can also include a delivery guide slidably disposable over the delivery shaft and having a distal end configured to engage a tissue scaffold disposed on the at least one prong on the distal end of the delivery shaft and to hold the tissue scaffold against a surface of bone.

In another embodiment, a tissue scaffold delivery system is provided that includes a delivery guide having an inner lumen extending therethrough and at least one tooth extending from a perimeter of a distal end thereof. The at least one tooth is configured to penetrate a tissue scaffold and to engage bone to hold a tissue scaffold in a fixed position relative to the bone. The delivery guide also includes at least one window adjacent to the distal end that is configured to enable viewing of a component disposed within the inner lumen at the distal end.

The tissue scaffold delivery system can have a variety of modifications. For example, the at least one window can include a plurality of cut-outs formed in the delivery guide and/or a transparent portion formed in the delivery guide. In some embodiments, the delivery guide can include an alignment mechanism configured to position a tool inserted therethrough in a predetermined radial position relative to the delivery guide. The tissue scaffold delivery system can include a punch tool configured to be advanced through the inner lumen of the delivery guide and to prepare bone for attachment of a tissue scaffold thereto. The bone preparation tool can include a punch tool that has at least one prong configured to punch at least one hole through a tissue scaffold held by the at least one prong and into bone underlying the tissue scaffold. For another example, the tissue scaffold delivery system can include a scaffold seating tool configured to be advanced through the inner lumen of the delivery guide. The scaffold seating tool can include a fastener-applying tool having a fastener-retaining member on a distal end thereof and can be configured to retain at least one fastener and to apply the fastener through a tissue scaffold held in position by the at least one tooth to fasten the tissue scaffold to a bone underlying the tissue scaffold. For yet another example, the tissue scaffold delivery system can include a delivery shaft having at least one prong extending from a distal end thereof. The at least one prong can be configured to extend through a tissue scaffold, and the delivery guide can be disposable over the delivery shaft such that the at least one tooth is configured to engage a tissue scaffold disposed on the at least one prong of the delivery shaft. In some embodiments, the tissue scaffold delivery system can include a delivery cannula having a funnel coupled to a distal end thereof, the delivery shaft being slidably disposable through the delivery cannula.

In another aspect, a method for loading a tissue scaffold onto a delivery shaft is provided that includes positioning a tissue scaffold on a surface of a loading block such that the tissue scaffold is disposed over at least one opening formed in the surface, and advancing at least one prong extending from a distal end of a delivery shaft along at least one channel formed in a guide member on the loading block. The at least one channel guides the at least one prong through the tissue scaffold and into the at least one opening.

The method can have any number of variations. For example, the guide member can guide the at least one prong through the tissue scaffold at a predetermined location relative to a perimeter of the tissue scaffold. For another example, the at least one opening can include at least one elongate slot, and the method can further include sliding the at least one prong through the at least one slot and removing the at least one prong from the at least one slot with the tissue scaffold attached thereto. In some embodiments, positioning a tissue scaffold on a surface of a loading block can include abutting a perimeter of the tissue scaffold against a surface of the guide member and/or positioning at least a portion of the tissue scaffold underneath at least a portion of the guide member. A surface of the tissue scaffold having viable tissue cells disposed thereon can be positioned in contact with the surface of the loading block.

In another aspect, a method for delivering a tissue scaffold is provided that includes advancing a proximal end of a delivery shaft into a distal end of a delivery cannula to position a tissue scaffold disposed on a distal end of the delivery shaft within the distal end of the delivery cannula. The delivery cannula causes the tissue scaffold to fold around at least one prong on the distal end of the delivery shaft as the tissue scaffold is advanced into the distal end of the delivery cannula.

The method can have any number of variations. For example, the tissue scaffold can include viable tissue cells disposed on a first surface thereof. The first surface can be prevented from coming into contact with an inner surface of the delivery cannula when the tissue scaffold is folded to thereby protect the viable tissue cells. For another example, the delivery cannula can include a funnel on the distal end thereof that folds the tissue scaffold. For yet another example, the method can include advancing the cannula into a body of a patient with the tissue scaffold and delivery shaft disposed therein, and positioning the at least one prong on the delivery shaft against bone to position the tissue scaffold. In some embodiments, the method can also include removing the cannula leaving the delivery shaft and tissue scaffold extending into a body of a patient, and advancing a delivery guide over the delivery shaft to cause a distal end of the delivery guide to engage the tissue scaffold and engage the bone, thereby holding the tissue scaffold in a fixed position against the surface of the bone. The method can further include removing the delivery shaft leaving the delivery guide extending into a body of a patient and holding the tissue scaffold against the surface of bone, and advancing a punch tool through the delivery guide, through the tissue scaffold, and into the bone to form at least one hole in the bone. The punch tool can optionally be viewed through at least one window formed in the delivery guide adjacent to the distal end of the delivery guide. The delivery guide can have an alignment mechanism that aligns the punch tool at a predetermined radial orientation relative to the delivery guide. The method can also include removing the punch tool from the delivery guide and inserting a fastener-applying tool through the delivery guide to insert at least one fastener through the tissue scaffold and into the at least one hole formed in the bone by the punch tool. The delivery guide can have an alignment mechanism that aligns the fastener-applying tool at a predetermined radial orientation relative to the delivery guide.

In another embodiment, a method for delivering a tissue scaffold is provided that includes positioning a distal end of a delivery guide on a tissue scaffold and against a surface of bone to hold a tissue scaffold at a fixed position relative to the surface of the bone, and advancing a fastener-applying tool through the delivery guide to insert a fastener through the tissue scaffold and into the bone, thereby fastening the tissue scaffold to the bone at the fixed position.

The method can vary in any number of ways. For example, positioning a distal end of the delivery guide can include penetrating at least one tooth on the delivery guide through the tissue scaffold and into the bone. For another example, the method can include, prior to advancing a fastener-applying tool through the delivery guide, advancing a punch tool through the delivery guide to form at least one hole through the tissue scaffold and into the bone for receiving the at least one fastener. In some embodiments, an alignment feature on the delivery guide can align the fastener-applying tool at a predetermined radial orientation relative to the delivery guide. For still another example, the method can include, prior to positioning a distal end of a delivery guide, positioning the tissue scaffold against the surface of bone using a delivery shaft. The delivery guide can be advanced over the delivery shaft to position the distal end of the delivery guide on the tissue scaffold and against the surface of the bone.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
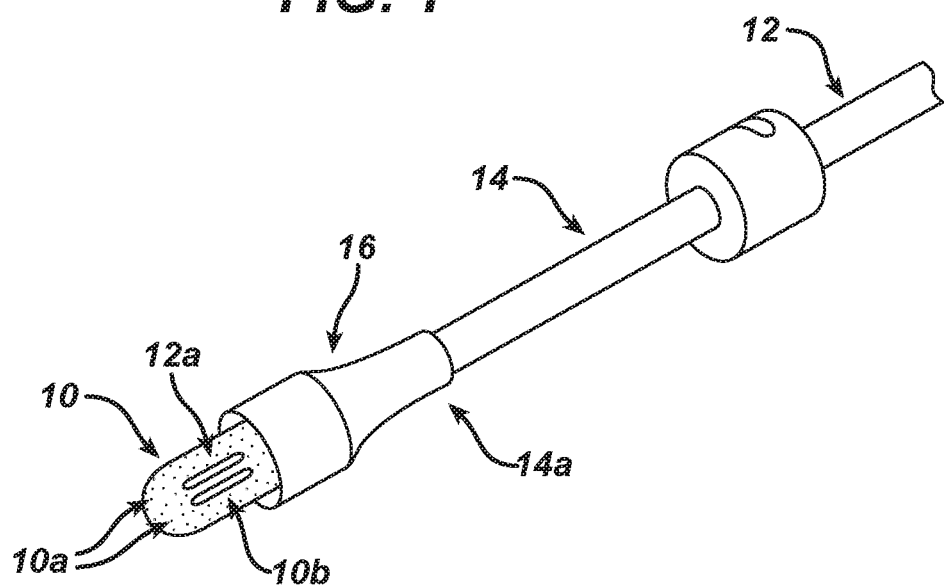
FIG. 1 is a partial perspective view of one embodiment of a delivery system that includes a delivery shaft having a tissue scaffold attached thereto being proximally advanced into a cannula having a funnel at a distal end thereof.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides various methods and devices for delivering and affixing implants. In general, various tools and techniques are disclosed for delivering a tissue scaffold to a cavity formed at a defect site in tissue, e.g., cartilage. In one embodiment, a delivery shaft is provided for engaging a scaffold and delivering the scaffold arthroscopically to a defect site in tissue. A loading block is provided and can be used to facilitate loading of the scaffold onto the delivery shaft, and a cannula is provided for containing and protecting the scaffold during delivery. Once the scaffold is delivered to a defect site, various additional devices can be used to affix the scaffold within a cavity formed in the tissue at the defect site. For example, in one embodiment a delivery guide is provided for holding the scaffold within the cavity, for example during removal of the delivery shaft and during attachment of the tissue scaffold to bone. A punch tool is also provided for forming one or more holes in bone through the scaffold, and a fastener-applying tool is provided for delivering a fastener to the scaffold to attach the scaffold to bone. The punch and fastener-applying tools can be configured to be inserted through the delivery guide. The present invention thus provided a variety of tools that can be used together in various combinations to aid in delivery and attachment of a tissue scaffold to a cavity formed at a defect site in tissue.

A person skilled in the art will appreciate that the term "tissue" as used herein is intended to encompass a variety of materials, e.g., cartilage, organs, and any other material that can be repaired using a tissue scaffold, and that the term "cartilage" as used herein can refer to any type of cartilage, e.g., hyaline cartilage, fibrocartilage, and elastic cartilage. A person skilled in the art will also appreciate that the term "defect site" as used herein is intended to encompass a current or former location of tissue that is damaged, unhealthy, or is otherwise undesirable and intended for repair with an implant. A person skilled in the art will also appreciate that the term "tissue replacement," "implant," "scaffold," or "matrix" as used herein is intended to encompass any surgically safe implant that is configured to be implanted in a patient to allow for tissue repair and regrowth.

A person skilled in the art will also appreciate that while the methods and devices are described in connection with minimally invasive arthroscopic procedures in which surgical devices are introduced percutaneously into a body cavity through a small opening formed in a patient, the methods and devices disclosed herein can be used in numerous surgical procedures and with numerous surgical instruments, including mini-open and open surgical procedures. A person skilled in the art will also appreciate that while the methods and devices are described in connection with chondral cartilage repair, the methods and devices can be used in other tissue repairs related to the knee, e.g., cartilage at the patella, or to other articulating surfaces, e.g., shoulder, ankle, hip, and elbow, and in any other type of tissue repair using a tissue replacement implant.

In an exemplary embodiment, a patient having a cartilage lesion at a defect site at the articular surface of a bone joint, such as the femoral condyle at the knee, can be prepared for tissue repair surgery. Through an arthrotomy incision, the knee joint can be opened and the defect site exposed. The size and shape of the lesion can vary, although a lesion at the femoral condyle traditionally has an elliptical shape having a surface area of about 3 $cm^2$ (300 $mm^2$). The undesirable cartilage tissue, which can include fibrillations and fissures, can be removed, to form a cavity in the tissue. An amount of healthy cartilage adjacent the lesion can also be removed in the process of removing the lesion. Debridement of the articular surface can be deep enough to expose a calcified layer of cartilage and/or a subchondral bone surface, e.g., in a range of about 2 to 3 mm below a top surface of the cartilage, for receiving a tissue repair implant. The bone surface can provide a substantially smooth surface for placement of the implant and a stable structure to which the implant can be attached. Once the articular surface has been properly prepared, the tissue repair implant can be implanted into the cavity formed in the cartilage and onto the articular surface. In some embodiments, a portion of the bone can be removed, and the implant can be implanted into the cavity formed in the cartilage and in the bone.

Before the implant is placed into a patient, the implant can be created using viable tissue, e.g., living, non-destroyed tissue cells, harvested from the patient in a first surgical procedure separate from a surgical procedure in which the implant is delivered to the patient, such as in autologous chondrocyte implantation (ACI) procedure, e.g., a procedure using a MACI® implant (available from Genzyme Corporation of Cambridge, Mass.). Although, a person skilled in the art will appreciate that the viable tissue can also or instead be gathered during the same surgical procedure in which the implant is attached to the patient.

Viable tissue can be collected from the patient in any way, as will be appreciated by a person skilled in the art. Various non-limiting embodiments of methods and devices for collecting tissue from a patient, such as in a biopsy procedure, can be found in U.S. Pat. No. 7,115,100 issued Oct. 3, 2006 entitled "Tissue Biopsy And Processing Device," U.S. Patent Publication No. 2008/0234715 filed Mar. 27, 2008 entitled "Tissue Extraction and Collection Device," and U.S. Patent Publication No. 2005/0059905 filed Sep. 11, 2003 entitled "Tissue Extraction and Maceration Device," which are hereby incorporated by reference in their entireties.

The source of viable tissue can vary, and the tissue can have a variety of configurations, but in an exemplary embodiment the harvested tissue includes chondrocytes. In an exemplary embodiment, once a sample of viable tissue has been obtained, the tissue sample can be processed under sterile conditions to create a suspension having at least one minced, or finely divided tissue particle. It is also possible to harvest the tissue in minced form such that further processing is not necessary. A person skilled in the art will appreciate that minced viable tissue fragments are simply small portions of living, non-destroyed tissue and that minced tissue fragments can enhance the effectiveness of the regrowth and healing response. The particle size of each tissue fragment can vary. By way of non-limiting example, the tissue size can be in the range of about 0.001 to 3 mm$^3$, but preferably the tissue particle is less than about 1 mm$^3$. In another embodiment, the viable tissue can be in the form of a tissue slice or strip harvested from healthy tissue that contains viable cells capable of tissue regeneration and/or remodeling, as described in U.S. Patent Publication No. 2005/0125077 filed Dec. 5, 2003 and entitled "Viable Tissue Repair Implants and Methods of Use," which is hereby incorporated by reference in its entirety. The tissue slice can be harvested to have a geometry that is suitable for implantation at the site of the injury or defect, and the harvested tissue slice can be dimensioned to allow the viable cells contained within the tissue slice to migrate out and proliferate and integrate with tissue surrounding the repair site. A person skilled in the art will appreciate that tissue can be collected from the patient and/or a compatible donor, that the tissue can be artificial tissue material, and that any combination of harvested tissue and artificial tissue material can be used.

Viable tissue harvested from a patient can optionally be combined with a variety of other materials, including carriers, such as a gel-like carrier or an adhesive. The viable tissue can also be contacted with a matrix-digesting enzyme to facilitate tissue migration out of the extracellular matrix surrounding the viable tissue. The enzymes can be used to increase the rate of cell migration out of the extracellular matrix and into the implant. Various non-limiting embodiments of gel-like carriers, adhesives, and enzymes can be found in U.S. Patent Publication No. 2005/0177249 filed Feb. 9, 2004 entitled "Scaffolds With Viable Tissue," which is hereby incorporated by reference in its entirety. Other non-limiting embodiments of viable tissue sources and methods for preparing viable tissues are disclosed in U.S. Patent Publication No. 2005/0113937 filed on Nov. 26, 2003 entitled "Conformable Tissue Repair Implant Capable Of Injection Delivery," which is hereby incorporated by reference in its entirety.

The viable tissue and any material combined with the viable tissue can be loaded onto a tissue scaffold. The scaffold can have a variety of configurations, as will be appreciated by a person skilled in the art. Generally, the scaffold can be formed using virtually any material or delivery vehicle that is biocompatible, bioimplantable, easily sterilized, and that has sufficient structural integrity and/or physical and mechanical properties to effectively provide for ease of handling in an operating room environment and to permit it to accept and retain one or more securing mechanisms, e.g., sutures, staples, adhesive, etc., without substantially tearing. By way of non-limiting example, the scaffold can be in the form of a matrix that is formed from a variety of any one or more materials, including resorbable materials, non-biological materials, and/or synthetic materials. The scaffold can be flexible so as to allow the scaffold to conform to the shape and dimensions of the target site of implantation. The scaffold can also include a bioabsorbable and/or bioresorbable component to act as a temporary carrier to improve handling of the implant during transportation. Various non-limiting embodiments of tissue scaffolds can be found in previously mentioned U.S. Patent Publication No. 2005/0177249 filed Feb. 9, 2004 entitled "Scaffolds With Viable Tissue," and in U.S. Patent Publication No. 2004/0078090 filed Feb. 25, 2003 entitled "Biocompatible Scaffolds With Tissue Fragments," U.S. Patent Publication No. 2005/0038520 filed Aug. 11, 2003 entitled "Method And Apparatus For Resurfacing An Articular Surface," and U.S. Pat. No. 6,884,428 issued Apr. 26, 2005 entitled "Use of Reinforced Foam Implants with Enhanced Integrity For Soft Tissue Repair And Regeneration," which are hereby incorporated by reference in their entireties.

Tissue harvested from a patient can be prepared and applied to a scaffold in any way, as will be appreciated by a person skilled in the art. The tissue component can be added to the scaffold during or after manufacture of the scaffold or before or after the implant is installed in a patient. Optionally, a bioactive agent can be incorporated within and/or applied to the tissue scaffold, and/or it can be applied to the viable tissue. Preferably, the bioactive agent is incorporated within, or coated on, the scaffold prior to the addition of viable tissue to the scaffold. The bioactive agent(s) can be selected from among a variety of effectors and cells that, when present at the site of injury, promote healing and/or regeneration of the affected tissue. Various non-limiting embodiments of effectors and cells can be found in previously mentioned U.S. Patent Publication No. 2005/0177249 filed Feb. 9, 2004 entitled "Scaffolds With Viable Tissue." Various non-limiting embodiments of applying tissue, e.g., minced viable tissue, to a scaffold can be found in U.S. Patent Publication No. 2004/0193071 filed Mar. 28, 2003 entitled "Tissue Collection Devices And Methods," which is hereby incorporated by reference in its entirety.

As mentioned above, once a tissue scaffold is available for implantation into a patient, the patient can be prepared for the scaffold's implantation by removing defective cartilage to create a hole or cavity in the cartilage that extends from a surface of the cartilage to the underlying femoral condyle, or other site, as mentioned above. The defect site can be prepared for scaffold implantation in a variety of ways. In one exemplary embodiment, a surgical cutting tool configured to cut a predetermined shape in tissue can be arthroscopically used to form a cut having a predetermined shape in the cartilage such that the cut shape encloses the lesion. Cartilage can be removed from within the cut shape such that the cut shape can define a perimeter of the tissue cavity in which the scaffold can be implanted. In some embodiments, the cutting tool can be used to cut multiple shapes in the cartilage, each of the shapes overlapping at least a portion of the lesion and optionally overlapping at least one additional cut shape. The shapes can also be altered and/or connected using the same and/or additional cutting tools. The cartilage within the combined cut shape can be removed to define the shape of the scaffold-receiving cavity. Various non-limiting embodiments of preparing tissue, including forming a scaffold-receiving cavity in tissue, can be found in U.S. patent application Ser. No. 12/412,492 entitled "Methods And Devices For Preparing And Implanting Tissue Scaffolds" filed on Mar. 27, 2009, which is hereby incorporated by reference in its entirety. A person skilled in the art will appreciate that other cutting tools or free-hand techniques can be used to prepare the defect site.

With defective tissue cleared as desired to form a cavity, an implant can be prepared for delivery to and optionally fastening within the cavity. An implant is traditionally created larger than an expected size of the cavity, e.g., a size larger than the defect site, and cut during the surgical procedure to a size and shape substantially matching the cavity. In this way, the implant can be cut from a portion of the prepared tissue replacement implant that includes a high concentration of deposited viable tissue, as tissue often adheres in varying concentrations across a tissue replacement implant. Moreover, the size of the cavity formed during a surgical procedure can be greater or less than expected, e.g., if the defect site is larger than previously determined, if more healthy tissue is removed than originally intended, etc. Cutting an implant to size during the procedure can thus help match the implant's size to the cavity's actual size.

The tissue replacement implant can be trimmed to a desired size and shape in any number of ways. In one exemplary embodiment, a tissue replacement implant can be cut from a larger prepared implant using a cutting tool configured to cut a predetermined shape that corresponds to a predetermined shape cut in tissue at the defect site. In another exemplary embodiment, a template tool can be used to size the defect and help cut a desirably sized tissue replacement implant. The template tool can have a variety of configurations, e.g., an adjustable template tool having at least one adjustable opening or a flexible film, and can be used in a variety of ways to size an implant. Various non-limiting embodiments of methods and devices for trimming a tissue scaffold to a desired size and shape can be found in previously mentioned U.S. patent application Ser. No. 12/412,492 entitled "Methods And Devices For Preparing And Implanting Tissue Scaffolds" filed on Mar. 27, 2009.

Regardless of how a cavity is formed in tissue and regardless of how a tissue replacement implant is created and cut to a desired size to fit in the cavity, the implant can be delivered into the cavity and affixed to bone and/or calcified cartilage in any way. In an exemplary embodiment, illustrated in FIG. 1, tools configured to deliver a tissue scaffold 10 to a site of attachment can include a delivery shaft 12 configured to be slidably received in a delivery cannula 14 having a funnel 16 removably coupled to a distal end 14a thereof. As discussed further below, the funnel 16 can be configured to move the scaffold 10 attached to a distal end 12a of the shaft 12 from a planar configuration outside the cannula 14 to a U-shaped folded configuration inside the cannula 14. With at least a portion of the shaft 12 having the scaffold 10 attached thereto disposed inside the cannula 14, the cannula 14 can be inserted into a body of a patient. The shaft 12 can be distally advanced through the cannula 14, thereby distally advancing the scaffold 10 out of the distal end 14a of the cannula 14 and into the patient. Advancing the scaffold 10 from the cannula 14 can also move the scaffold 10 from the folded configuration to the planar configuration in which the scaffold 10 can be attached to a tissue defect site.

Although the tissue scaffold 10 is illustrated as having an oblong shape and as a tissue matrix having viable tissue disposed on one side thereof and having a plurality of pores 10a formed therethrough, the scaffold 10 can have a variety of shapes, sizes, and configurations. In some embodiments, the scaffold 10 can have a thickness of less than about 3 mm and a surface area of about 10 cm$^2$ (1000 mm$^2$) to conform to a traditionally-sized tissue defect site.

Figure 2A:
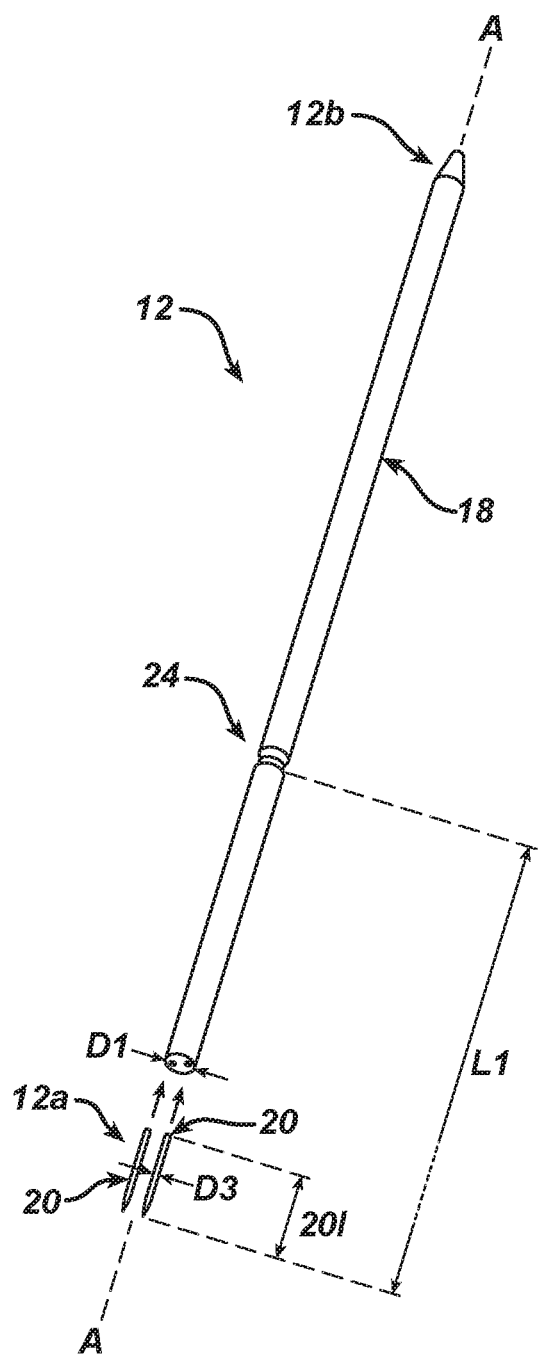
FIG. 2A is an exploded perspective view of the delivery shaft of FIG. 1.
Figure 2B:
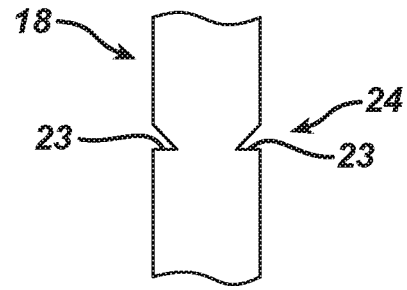
FIG. 2B is a cross-sectional view of one embodiment of a locking mechanism formed in the delivery shaft of FIG. 2A.
Figure 3:
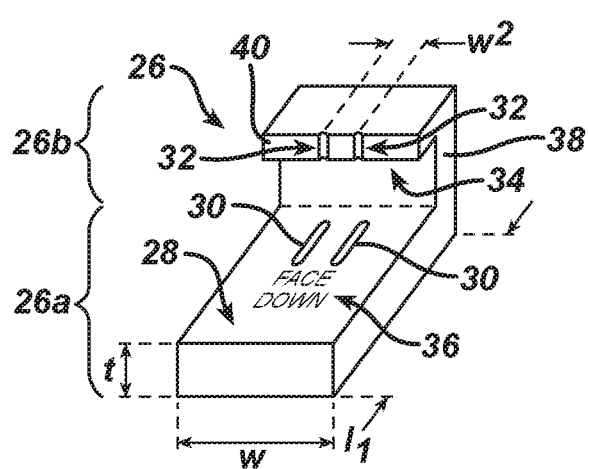
FIG. 3 is a perspective view of one embodiment of a loading block.
Figure 4:
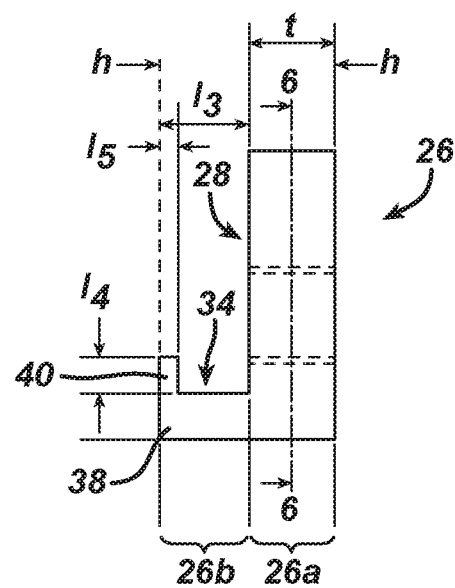
FIG. 4 is a side view of the loading block of FIG. 3.
Figure 5:
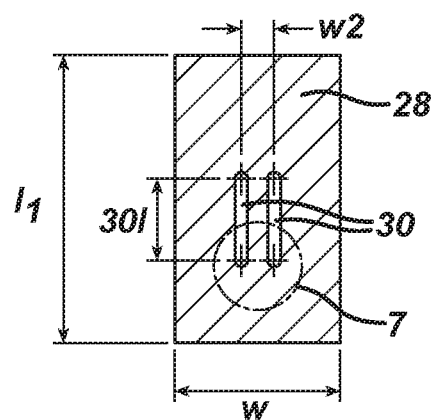
FIG. 5 is a top view of the loading block of FIG. 3.
Figure 6:
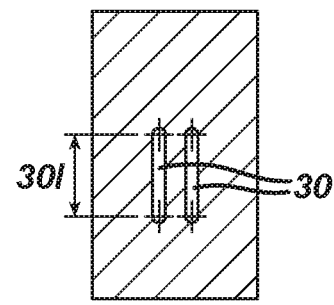
FIG. 6 is a top view of a cross-section of a main body of the loading block of FIG. 4.
Figure 7:
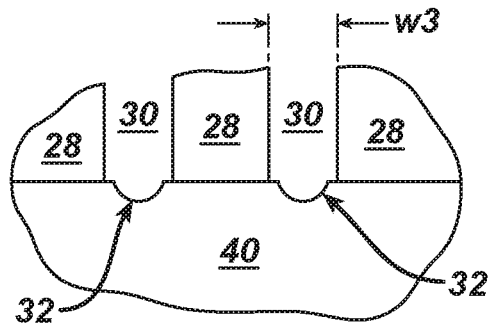
FIG. 7 is an enlarged top view of the loading block of FIG. 5.
Figure 10:
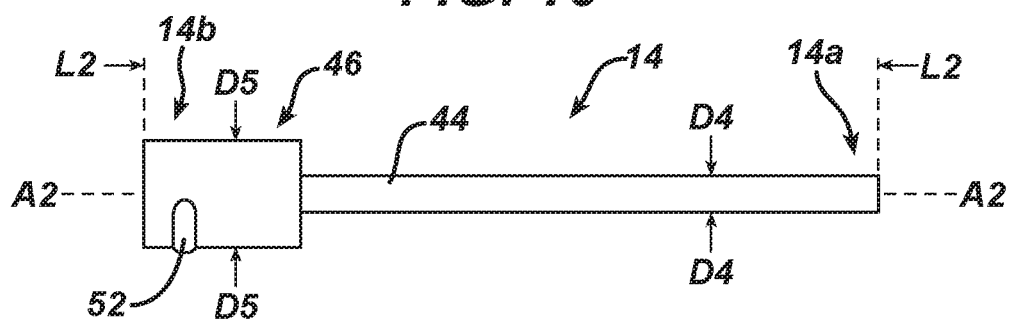
FIG. 10 is a side view of the cannula of FIG. 1.
Figure 11:
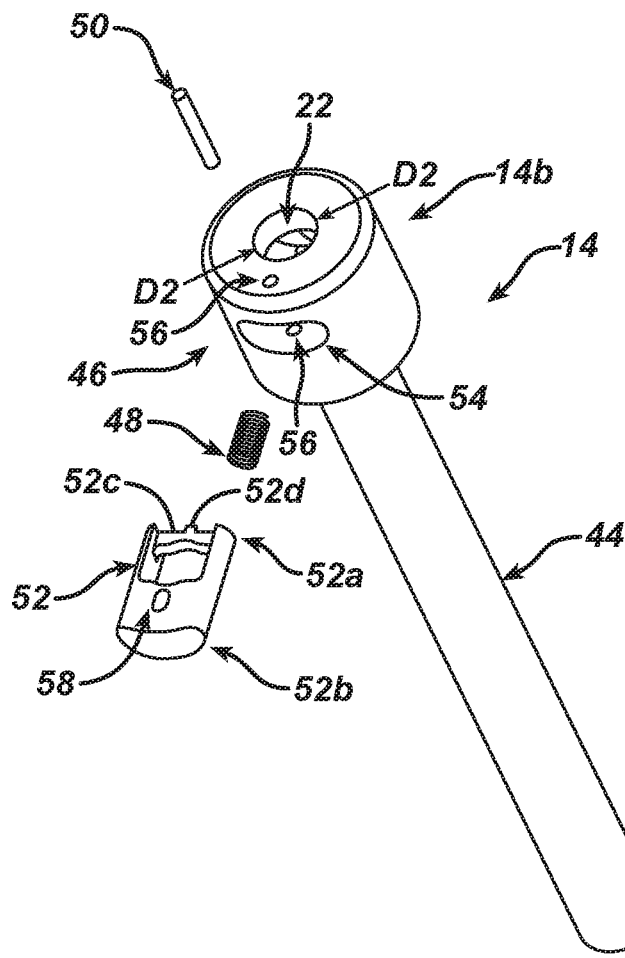
FIG. 11 is an exploded perspective view of the cannula of FIG. 10.

The delivery shaft 12 can also have a variety of sizes, shapes, and configurations. In this embodiment, shown in FIGS. 2A and 2B, the delivery shaft 12 can be configured similar to a fork and it can include an elongate body 18 having at least one prong 20 at the distal end 12a of the shaft 12. The shaft 12 can have any longitudinal length, but in an exemplary embodiment the shaft 12 can be longer than the cannula 14 to allow the shaft 12 to be disposed in an inner lumen or passageway 22 extending through the cannula 14 and simultaneously distally extend beyond the cannula's distal end 14a and proximally extend beyond a proximal end 14b of the cannula 14 (see FIGS. 10 and 11). A proximal end 12b of the elongate body 18 can have a tapered cone shape, e.g., be tapered in proximal direction, as shown, to help introduce the shaft 12 proximal end 12b first through the funnel 16 in the distal end 12a of the cannula 12, as discussed further below. One or more portions of the shaft 12 can optionally include one or more gripping mechanisms, e.g., molded finger depressions, treads, etc., to facilitate handling and manipulation of the shaft 12.

The one or more prongs 20 at the shaft's distal end 12a can generally be configured to penetrate and extend through a tissue scaffold, e.g., the scaffold 10, to attach the scaffold 10 to the shaft 12 for delivery into a body of a patient. The one or more prongs 20 can have any size, shape, and configuration and can be configured with sufficient strength such that the shaft 12 can serve as a bone preparation tool. In an exemplary embodiment, each prong 20 has a longitudinal length 20l greater than a thickness of a tissue scaffold to which the prong 20 is configured to be attached, and more preferably the length 20l of each prong 20 is sufficient to allow the scaffold to fold around the prongs 20 without the scaffold falling off, as discussed further below. In an exemplary embodiment, the length 20l of each prong 20 is in a range of about 15 to 35 mm. In an exemplary embodiment, each of the prongs 20 also has a diameter D3 that is equal to or less than a diameter of a tissue scaffold to which the prongs 20 are configured to be attached to help prevent the prongs 20 from damaging the scaffold. In an exemplary embodiment, the diameter D3 of the prongs 20 is in a range of about 0.1 to 2 mm, e.g., about 0.5 to 1 mm. Although two prongs 20 are shown, the delivery shaft 12 can include any number of prongs 20. Moreover, each of the prongs 20 can be the same or different from any other of the prongs 20. The prongs 20 can be configured as spikes or pins as shown, with or without tapered distal tips configured to help the prongs 20 penetrate a tissue scaffold. The prongs 20 can be arranged at the shaft's distal end 12a in any configuration, such as equidistantly spaced radially around a central longitudinal axis A of the shaft 12, as illustrated. In an embodiment where the shaft 12 has a single prong, the single prong can be substantially axially aligned with the central longitudinal axis A, or in other embodiment it can be offset from the axis A.

Although the prongs 20 are shown integrally formed with the elongate body 18 (they appear detached in the exploded view shown in FIG. 2A), any one or more of the prongs 20 can be movably coupled to the elongate body 18. In some embodiments, the prongs 20 can be retractable such that in an extended position the prongs 20 can extend distally beyond the elongate body's distal end and in a retracted position can be contained within the elongate body 18. Retraction and extension of movable prongs can be controlled in any way, as will be appreciated by a person skilled in the art, such as through actuation of a control mechanism, e.g., a knob, a button, a lever, an electronic signal communicator, etc., at the proximal end 12b of the shaft 12. Alternatively or in addition to being retractable, the one or more prongs 20 can be modular elements configured to be removably coupled to the elongate body 18 in any way appreciated by a person skilled in the art, e.g., threadably attached, snap fit, etc. In this way, prongs of different sizes, e.g., having different diameters, can be coupled to the elongate body 18 to allow the shaft 12 to more effectively attach to various tissue scaffolds during the same or different surgical procedures. Modular prongs can optionally be supplied with a delivery shaft as part of a kit, which can also include a delivery cannula and a funnel.

Although the shaft 12 can be a solid member as shown, the shaft 12 can include one or more passageways formed therethrough. For non-limiting example, the shaft 12 can include a tunnel extending through its distal and proximal ends 12a, 12b that is configured to receive at least one surgical instrument disposed therethrough, e.g., a vacuum device configured to suction fluid, tissue, etc. away from a surgical site.

The shaft 12 can also optionally include a locking feature 24 located between the distal and proximal ends 12a, 12b and configured to be engaged by a corresponding locking mechanism on the cannula 14, discussed below, to retain the shaft 12 at a predetermined position within a passageway 22 of the cannula 14. The locking feature 24 can be located anywhere along a longitudinal length of the shaft 12. To help position the at least one prong 20 within the cannula 14, a longitudinal length L1 between a distal-most end of the shaft 12 and the locking feature 24 can be less than a longitudinal length between a distal-most end of the cannula 14 and the cannula's locking mechanism.

The locking feature 24 can have a variety of shapes, sizes, and configurations. In the illustrated embodiment, the locking feature 24 is in the form of an annular groove formed in a surface of the elongate body 18 around a circumference of the body 18. The groove can be tapered to prevent movement of the shaft 12 within the cannula 14 when the locking feature 24 is engaged by its cannula counterpart. Because in the illustrated embodiment the shaft 12 is configured to be advanced proximal end 12b first into the distal end 14a of the cannula 14 and advanced through the passageway 22 proximally to load the shaft 12 therein, the groove tapers outward in a distal to proximal direction to form a perpendicular stop surface 23 that stops proximal movement of the shaft 12 when the locking feature 24 is engaged by its cannula counterpart. The proximal tapering can also allow the shaft 12 to be advanced distally when distal pressure is applied thereto, as discussed further below. A person skilled in the art will appreciate that while the locking feature 24 can be a radial groove formed around a circumference of the elongate body 18 as shown, various other locking techniques can be used and can be formed on any portion of the shaft 12 and/or cannula 14.

The locking feature 24 can be configured to be engaged by a corresponding locking mechanism, discussed further below, formed on or otherwise coupled to the cannula 14 when the shaft 12 is advanced into the cannula 14. The locking mechanism and the locking feature 24 can thereby releasably lock the shaft 12 in the passageway 22 at a predetermined location relative to the cannula 14. In this way, the at least one prong 20 configured to attach to a tissue scaffold can be predictably and effectively contained within the passageway 22 for safe delivery into a body of patient.

The tissue scaffold 10 can be attached to the distal end 12a of the shaft 12 in a variety of ways, as will be appreciated by a person skilled in the art. In one embodiment, a grasper can hold the scaffold 10 as the prongs 20 of the shaft 12 are passed through the scaffold 10. A person skilled in the art will appreciate that the term "grasper" as used herein is intended to encompass any surgical instrument that is configured to grab and/or hold the scaffold 10 such as forceps, retractors, movable jaws, magnets, adhesives, etc. In another embodiment, a loading block can be used to help predictably position the prongs 20 relative to the scaffold 10. FIGS. 3-7 illustrate one exemplary embodiment of a loading block 26 configured to help attach the tissue scaffold 10 to the delivery shaft 12.

Generally, the loading block 26 can include a main body 26a and a guide member 26b positioned at least partially above the main body 26a. The main body 26a can include a top, tissue-receiving surface 28 configured to receive a tissue scaffold thereon. The top surface 28 can have one or more openings 30 formed therein that extend at least partially through a thickness t of the main body 26a and that are each configured to receive a prong of a delivery shaft therein. When a tissue replacement implant is placed on the top surface 28, the prongs can be guided through one or more channels 32 formed in a portion of the guide member 26b positioned over the main body 26a and can thereby be guided through the scaffold and at least partially into the openings 30. The delivery shaft with the scaffold attached thereto can then be removed from the loading block 26 and used to introduce the scaffold into a body of a patient, as discussed further below.

While the loading block 26 can be made from any combination of rigid and/or flexible materials, in an exemplary embodiment the block 26 is composed of one or more rigid materials, e.g., Radel R® polyphenylsulfone available from Solvay Advanced Polymers, L.L.C. of Alpharetta, Ga., so the block 26 does not deform during use, which can improve chances of stable, predictable scaffold loading using the block 26. The block 26 can have dimensions appropriate for use with any size tissue replacement implant and any size delivery guide to which the tissue replacement implant is to be attached using the block 26. In an exemplary embodiment, as illustrated, the block 26 has a longitudinal length $l_1$ of about 1.4 in. (35.6 mm), a width w of about 0.8 in. (20.3 mm), and a height h of about 0.85 in. (21.6 mm). The main body 26a and the guide member 26b of the loading block 26 can have a variety of sizes, shapes, and configurations. In the illustrated embodiment, the block 26 has a rectangular box-shaped main body 26a with an L-shaped guide member 26b extending from the top, tissue-receiving surface 28.

The top, tissue-receiving surface 28 of the main body 26a can have a variety of sizes, shapes, and configurations. The top surface 28 can have any shape and surface area that is generally large enough to receive a tissue scaffold thereon. The top surface 28 can be configured to be large enough such that edges of a scaffold placed thereon do not extend beyond any of the edges of the top surface 28 to help more stably position the scaffold on the block 26. The top surface 28 can in some embodiments have a surface area greater than about 3 cm$^2$ (300 mm$^2$). In the illustrated embodiment, the top surface 28 has a surface area of about 0.94 in.$^2$ (606 mm$^2$). The top surface 28 can be rectangular as shown, or it can have any other shape, e.g., elliptical, square, etc. The top surface 28 can be substantially planar to allow a tissue scaffold to rest substantially flat thereon. A person skilled in the art will appreciate that the top surface 28 can longitudinally extend in a single plane such that the main body 26a has a constant thickness t as shown, or the top surface 28 can extend at an angle in any direction or directions with the main body 26a having a varying thickness t. In the illustrated embodiment, the thickness t is about 0.42 in. (10.7 mm). If the top surface 28 is angled, it can angle towards the guide member 26b such that the thickness t of the main body 26a decreases toward the guide member 26b, which can help position an edge of a tissue scaffold on the top surface 28 against a facing surface 34 of the guide member 26b that faces the top surface 28, as discussed further below.

The openings 30 in the top surface 28 can also have any size, shape, and configuration. The openings 30 can be configured to receive the prongs 20 of the shaft 12, and can thus have a size large enough to accommodate entry of the prongs distal end first into the openings 30. The openings 30 can be separated by a distance w2, which is about 0.157 in. (4.0 mm) in this illustrated embodiment, and which corresponds to the distance between the prongs 20 on the delivery shaft 12. The distance w2 can, however, vary depending on the delivery shaft used therewith. As illustrated, the openings 30 are each configured as elongate oblong slots extending longitudinally along the top surface 28 and having a longitudinal length 30l of about 0.4 in. (10.2 mm) and a width w3 of about 0.065 in. (1.7 mm), although the openings 30 can have any orientation, size, and shape, e.g., circular, square, rectangular, etc. The openings 30 can also have any depth extending at least partially through the thickness t of the main body 26a and can generally be configured to be deep enough such that the penetration of the prongs 20 through the scaffold 10 is not limited. Although two openings 30 are illustrated in this embodiment, the block 26 can include any number of openings 30. Moreover, each of the openings 30 can be the same or different from any other of the openings 30. The block 26 can also include more openings 30 than a number of prongs that extend through a tissue replacement implant on the top surface 28.

The top surface 28 can optionally include a label 36 configured to provide information related to the loading block 26. Although the label 36 is shown as alphabetical characters printed, embossed, or otherwise viewable on the top surface 28, a person skilled in the art will appreciate that the label 36 can have any size, shape, and configuration, such as any combination of colors or alphabetical, numerical, and symbolic characters. A person skilled in the art will also appreciate that the block 26 can include any number of labels and that each label can be printed, embossed, or otherwise viewable on any portion of the loading block 26 in addition or in alternative to the top surface 28. In the illustrated embodiment, the label 36 identifies a suggested positioning of a tissue scaffold to be received thereon with written instructions to place a tissue scaffold on the top surface 28 with a tissue side of the scaffold face down, which can help in protecting viable tissue generally deposited on one side of the tissue scaffold during implantation of the tissue scaffold as discussed further below. Another non-limiting example of the label 36 includes dimensions of various components of the block 26, such as the top surface 28, the openings 30, and the channels 32.

As mentioned above, the guide member 26b extending from the main body 26a of the block 26 is L-shaped, although it can have a variety of sizes, shapes, and configurations. As illustrated in this embodiment, the guide member 26b includes a first arm 38 extending substantially perpendicular from the main body 26a, and a second arm 40 extending substantially perpendicular from the first arm 38 and extending over the main body 26a such that the second arm 40 is substantially parallel to the top surface 28 of the main body 26a. The location of the first arm 38 on the top surface 28 can vary, but in the illustrated embodiment the first arm 38 extends from a terminal end 28a of the top surface 28. Either of the first and second arms 38, 40 can have a longitudinal length longer than the other, or their longitudinal lengths can be the same, but in this illustrated embodiment the first arm 38 has a longer longitudinal length $l_3$ of about 0.43 in. (10.9 mm) than the second arm's longitudinal length $l_4$ of about 0.177 in. (4.5 mm). The second arm's longitudinal length $l_4$ can define a predetermined distance from a perimeter of the scaffold 10 placed on the top surface 28 that the prongs 20 of the delivery shaft 12 can be advanced through the scaffold 10. The second arm's longitudinal length $l_4$ can thus be configured to allow the scaffold 10 to fold around the prongs 20 when advanced into the cannula 14, as discussed further below. The longitudinal length $l_3$ can be selected in relation to a length of the prongs 20 if the shaft 12, so that a scaffold positioned on the block 26 ends up at a desired position on the prongs 20, e.g., about half length in this illustrated embodiment.

As previously indicated, the guide member 26 can also include one or more channels 32 formed therein for guiding the prongs 20 into the openings 30. The channels 32 formed in the guide member 26b can also have a variety of sizes, shapes, and configurations. Generally, the channels 32 can be configured to each receive a prong of a delivery shaft therein and guide the prong therethrough in a predetermined direction to a predetermined position, e.g., toward one of the openings 30 in the top surface 28. In this way, the prongs can be advanced through a scaffold on the top surface 28 at a predictable, desirable position.

The channels 32 can be axially aligned with the openings 30 in a one-to-one relationship where each channel 32 is associated with one opening 30. Although two channels 32 are illustrated in this embodiment to correspond with the two openings 30, the block 26 can include any number of channels 32 more or less than the number of openings 30 formed in the loading block 26. Moreover, each of the channels 32 can be the same or different from any other of the channels 32. The block 26 can include more channels 32 than a number of prongs on a delivery shaft that are extended through the guide member 26b and into a tissue replacement implant on the top surface 28. The channels 32 can be separated by the distance w2 equal to the distance separating the openings 30 to align the channels 32 with the openings 30. As illustrated, the channels 32 are each configured as semi-cylindrical cut-outs extending through the second arm 40 of the guide member 26a in a direction substantially perpendicular to a face of the top surface 28. The channels 32 can, however, have any size, shape, and orientation relative to the top surface 28. The channels 32 can have any depth extending into the guide member 40 configured to provide enough of a pathway along which a surgical tool can be guided. The channels 32 can also have any longitudinal length $l_5$, although they can be configured to be shorter than prongs of a delivery shaft to be received therein to allow at least a portion of the prongs to extend along the channels 32 and have their distal-most ends of the prongs received in the openings 30. As illustrated, the channels 32 can extend along one surface of the guide member 40 and have a longitudinal length $l_5$ equal to the width of the guide member's second arm 40, e.g., about 0.08 in. (2.0 mm).

Figure 8:
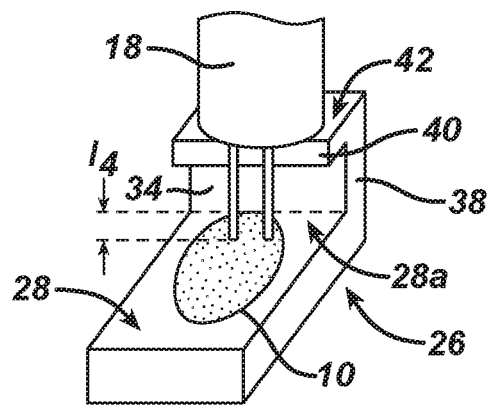
FIG. 8 is a partial perspective view of the tissue scaffold of FIG. 1 on a surface of the loading block of FIG. 3 and the delivery shaft of FIG. 2A using the loading block to advance prongs at a distal end of the delivery shaft through the tissue scaffold.

In use, as illustrated in one embodiment in FIG. 8, the block 26 can be used to attach the scaffold 10 to the prongs 20 of the delivery shaft 12. Using the block 26 to attach the scaffold 10 to the delivery shaft 12 can position the prongs 20 through the scaffold 10 at a predetermined location on the scaffold 10, thereby helping to safely deliver the scaffold 10 into the body of a patient, as discussed further below. Although use of the loading block 26 is described with reference to the scaffold 10 and the shaft 12 of FIG. 1, a person skilled in the art will appreciate that the loading block 26 can be used with these or any other implant and delivery device.

To prepare the scaffold 10 for attachment to the delivery shaft 12, the scaffold 10 can be positioned on the main body's top surface 10 in a substantially planar position. As discussed above, the scaffold 10 can be placed on the top surface 28 with a side of the scaffold 10 having viable tissue disposed thereon face down on the top surface 28 with another, opposite side of the scaffold 10 facing up. The scaffold 10 can be positioned anywhere on the top surface 28, but as shown in the illustrated embodiment, the scaffold 10 can be positioned such that a portion of its perimeter abuts the facing surface 34 of the guide member 26b at the terminal edge 28a of the top surface 28 where the top surface 28 meets the guide member 26b. The scaffold 10 can also be positioned with its major axis substantially parallel to longitudinal lengths of the openings 30. In this way, the scaffold 10 can be predictably positioned on the top surface 28 over the openings 30 and under the channels 32 with a predetermined length of the scaffold 10 extending between the terminal edge 28a and the openings 30, e.g., the longitudinal length $l_4$ of the second arm 40 underneath which the scaffold 10 can be positioned.

With the scaffold 10 positioned as desired on the top surface 28 of the block 26, the prongs 20 of the delivery shaft 12 can be distally advanced along the channels 32 toward the scaffold 10 and inserted through the scaffold 10 to attach the scaffold 10 thereto. In this way, each of the prongs 20 can be guided through the scaffold 10, optionally with distal-most tips of the prongs 20 helping to pierce the scaffold 10 and/or the prongs 20 passing through the pores 10a of the scaffold 10. Because the channels 32 can be axially aligned with the openings 30, the prongs 20 can each be received in one of the openings 30 after passing through the scaffold 10. The longitudinal lengths of the prongs 20 can be long enough to allow the prongs 20 to simultaneously extend through the channels 32 and at least partially into the openings 30. Distal movement of the shaft 12 can be limited by a stop mechanism, such as a bottom surface of one or more of the openings 30 and/or by a top surface 42 of the guide member 26b. The top surface 42 of the guide member 26b can stop distal movement of the shaft 12 when the distal surface of the elongate body 18 of the shaft 12, e.g., the surface of the body 18 from which the prongs 20 extend, contacts the guide member's top surface 42. By limiting distal movement of the shaft 12 in any one or more ways, the prongs 20 can be advanced through the scaffold 10 by a sufficient amount such that the scaffold 10 can be adequately attached to the prongs 20.

With the prongs 20 extending through the scaffold 10, the delivery shaft 12 can be disengaged from the block 26 with the scaffold 10 attached thereto. The shaft 12 can be moved in a direction away from the top surface 28 along the longitudinal axis A of the shaft 12 to disengage the prongs 20 from the openings 30 and hence the shaft 12 from the block 26. Optionally, the prongs 20 can be slid through the openings 30 in a direction away from the guide member 26b to help remove the shaft 12 and the scaffold 10 from the block 26, which can help ensure that the position of the scaffold 10 on the prongs 20 does not change during disengagement of the prongs 20 from the block 26. The prongs 20 can slide through the openings 30, such as in the illustrated embodiment, when the openings 30 are configured as elongate slots. By sliding the prongs 20 through the openings 30 away from the guide member 26b, the scaffold 10 can also be moved away from the guide member 26b and in particular out from underneath the second arm 40, thereby minimizing chances of the scaffold 10 hitting the second arm 40 when being removed from the top surface 28. Such sliding of the prongs 20 can thus be particularly effective before the shaft 12 is substantially moved in a direction along the longitudinal axis A of the shaft 12. Further, sliding the scaffold 10 in a substantially planar position rather than angling the scaffold 10 to avoid contact between the guide member 26b and the scaffold 10 can more carefully handle the fragile scaffold 10 and help retain viable tissue on the scaffold 10. The shaft 12 can optionally be slid in the openings 30 and pivoted against the second arm 40 to simultaneously slide and lift the scaffold 10.

Figure 9:
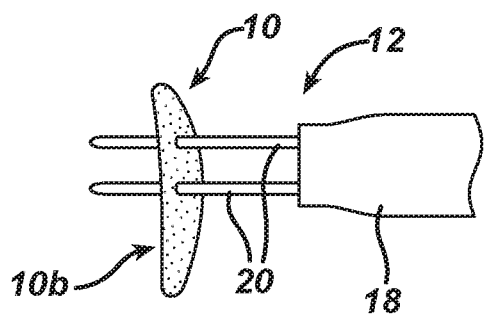
FIG. 9 is a partial side view of the tissue scaffold of FIG. 8 attached to the prongs of the delivery shaft.

With the scaffold 10 attached to the shaft 12 via the prongs 20, friction can hold the scaffold 10 on the prongs 20, as shown in FIG. 9, until the scaffold 10 is removed therefrom. The scaffold 10 attached to the shaft 12 can be delivered to a body cavity of a patient in a variety of ways, as will be appreciated by a person skilled in the art. In an exemplary embodiment, as mentioned above, the delivery shaft 12 with the scaffold 10 attached thereto can be disposed in the cannula 14 to deliver the scaffold 10 to a tissue defect site for implantation.

The cannula 14 can have a variety of sizes, shapes, and configurations. In the embodiment, shown in FIGS. 10 and 11, the cannula 14 has a longitudinal length L2 and includes an elongate body 44 having a head 46 at the proximal end 14b of the cannula 14. The cannula's elongate body 44 can be substantially cylindrical-shaped, as shown, although the elongate body 44 can have any shape. The elongate body 44 can also have any size such that its longitudinal length can allow at least a portion of the elongate body 44 to be inserted into a body cavity of a patient with at least the head 46 of the cannula 14 being located outside the patient. The inner passageway 22 of the cannula 14 can extend longitudinally through the elongate body 44 and can have any size and shape, e.g., cylindrically-shaped, that is configured to allow the delivery shaft 12 to be slidably disposed therein. The inner passageway 22 can have a constant diameter D2, or the passageway 22 can have a variable diameter D2, e.g., having a larger diameter D2 in at least a distal portion of the elongate body 44 to help accommodate the shaft 12 and the scaffold 10. The elongate body 44 can have a substantially constant outer diameter D4 as shown, or the distal end 14a of the elongate body 44 can have a tapered cone shape, e.g., be tapered in a distal direction, to help introduction of the cannula's distal end 14a first into a patient. One or more portions of the elongate body 44 and/or the head 46 can optionally include one or more gripping mechanisms, e.g., molded finger depressions, treads, etc., facilitate handling and manipulation of the cannula 14.

As mentioned above, the shaft 12 can be configured to be disposed in the cannula 14 with the shaft's elongate body 18 slidably received within the inner passageway 22 of the cannula 14. The shaft's elongate body 18 can thus, as shown in this embodiment, be substantially cylindrical-shaped to match the shape of the cannula's inner passageway 22. The corresponding cylindrical shapes in the cannula's passageway 22 and shaft's elongate body 18 can allow the shaft 12 to be both linearly and rotatably movable within the inner passageway 22, which can help position the scaffold 10 at a defect site, discussed further below. The shaft's elongate body 18 can thus have a diameter D1 less than the diameter D2 of the cannula's inner passageway 22 to allow the elongate body 18 to be movable therein.

The head 46 is illustrated as being located at a proximal-most end of the cannula 14, but the head 46 can be located anywhere at the cannula's proximal end 14b. The head 46 can be, for non-limiting example, substantially cylindrically-shaped as shown, although as will be appreciated by a person skilled in the art, the head 46 can have any size, shape, and configuration. The head 46 can serve as a handle configured to allow the cannula 14 to be manipulated outside the body of a patient. A diameter D5 of the head 46 can be larger than the diameter D4 of the elongate body 44, as shown, which can help the head 22 serve as a handle and help provide a locking mechanism configured to releasably hold the delivery shaft 12 in a fixed position in the passageway 22.

The cannula's locking mechanism can have a variety of shapes, sizes, and configurations but can generally be configured to complement and be effective with the shaft's locking feature 24 to releasably lock the shaft 12 within the cannula 14. In the illustrated embodiment, the cannula's locking mechanism includes a button 52 coupled to the head 46 of the cannula 14 using a pin 50 and a spring 48. The head 46 can have an opening 54 formed in a side surface thereof such that the opening 54 is in communication with the passageway 22 extending through the cannula 14. The button 52 can extend into the head 46 through the opening 54 with a distal end 52a of the button 52 positioned within the head 46 and with a proximal end 52b of the button 52 positioned outside the head 46. The spring 48 can be positioned within the head 46 and bias the button 52 toward the passageway 22. The pin 50 can extend through a hole 56 formed in the head 46 and a hole 58 formed in the button 52 to hold the button 52 within the opening 54. The hole 58 in the button 52 can have a diameter than larger than a diameter of the pin 50, which in addition to the spring-loading of the button 52, can allow the button 52 to be movable relative to the pin 50 and the head 46 when the button 52 is depressed. In this way, with the button 52 in a depressed, unlocked position, the passageway 22 can be clear and a surgical tool can be freely slidable therethrough. With the button 52 in a default, locked position, a locking member 52c of the button 52 can contact a surgical tool disposed within the passageway 22 in the head 46 to lock the surgical tool therein until the button 52 is moved to the unlocked position. The locking member 52c is shown as a cross-bar having a protrusion 52d formed thereon. An inner surface of the locking member 52c, which can have any size, shape, and configuration, can be configured to engage the locking feature 24 of the shaft 12, while the protrusion 52d can be configured to keep the spring 48 aligned.

As mentioned above, the shaft 12 with the scaffold 10 attached thereto can be advanced into the cannula 14 in a variety of ways. In an exemplary embodiment, shown in FIG. 1, the shaft 12 can be advanced proximal end 12b first into the distal end 14a of the cannula 14 to help minimize a length of the passageway 22 that the scaffold 10 passes through to help reduce chances of the scaffold 10 losing viable tissue by scraping against the passageway 22 and to help reduce chances of the scaffold 10 accidentally falling off the prongs 20 through jostling in the passageway 22. While the shaft 12 can be directly inserted into the cannula 14, in an exemplary embodiment, the shaft 12 can be advanced through the funnel 16 coupled to the distal end 14a of the cannula 14. The funnel 16 can be configured to have a tapering inner lumen or passageway to move the scaffold 10 from a planar configuration on the prongs 20, e.g., as illustrated in FIG. 9, to a folded configuration on the prongs 20 inside the cannula 14, as discussed further below.

Figure 12:
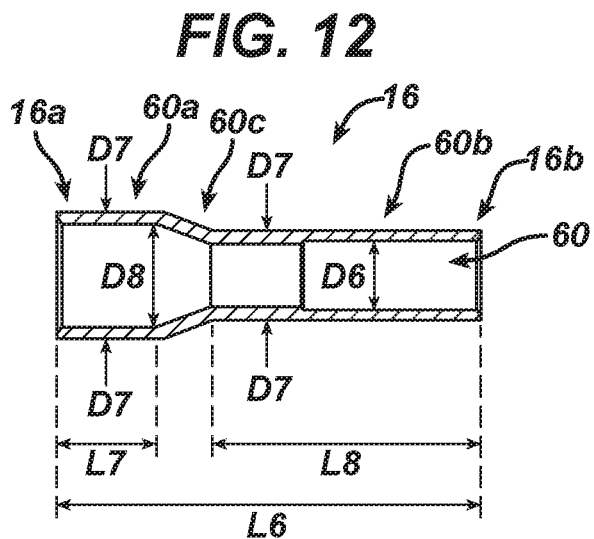
FIG. 12 is a cross-sectional side view of the funnel of the cannula of FIG. 1.
Figure 13:
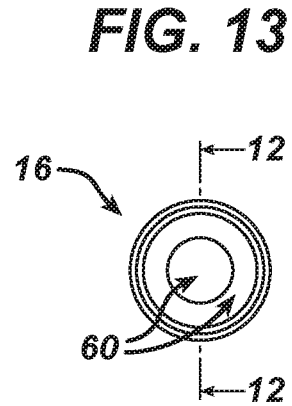
FIG. 13 is a distal end view of the funnel of FIG. 12.

The funnel 16 can have a variety of sizes, shapes, and configurations. In an exemplary embodiment, illustrated in FIGS. 12 and 13, the funnel 16 includes an elongate body having an inner lumen or passageway 60 extending between distal and proximal ends 16a, 16b thereof. The funnel 16 can have any longitudinal length L6, e.g., about 2.36 in. (59.9 mm), any length of which can be advanced over the cannula 14. The passageway 60 can have any shape, e.g., a generally cylindrical shape to correspond to the shape of the funnel's passageway 60 with the cannula's passageway 22. The passageway 60 can have a varying diameter such that a diameter D6 of the passageway 60 in a distal portion 60a of the passageway 60 is greater than the diameter D6 of the passageway 60 in a proximal portion 60b of the passageway 60, with the diameter D6 tapering proximally inward at a mid-portion 60c of the funnel 16 between the distal and proximal portions 60a, 60b. The distal and proximal portions 60a, 60b can each have any longitudinal length, e.g., a length L7 of about 0.54 in. (13.7 mm) in the distal portion 60a and a length L8 of about 1.5 in. (38.1 mm) in the proximal portion 60b. The diameter D6 of the passageway 60 in the proximal portion 60b of the funnel 16 can be slightly greater than the outer diameter D4 of the cannula 14 at least at the distal end 14a of the cannula 14 to allow the proximal end 16b of the funnel 16 to securely fit over the distal end 14a of the cannula 14, as illustrated in FIG. 1, such that the funnel's passageway 60 and the cannula's passageway 22 can be in communication with each other and can provide a smooth transition between the two. The size of the diameter D6 of the funnel's passageway 60 can vary, e.g., about ⅔ larger in the distal portion 60a with a diameter D6 of, e.g., about 0.575 in. (14.6 mm) in the distal portion 60a and about 0.377 in. (9.6 mm) in the proximal portion 60b. An outer diameter D7 of the funnel's elongate body can vary, e.g., about 0.688 in. (17.5 mm) in the distal portion 60a and about 0.48 in. (12.2 mm) in the proximal portion 60b, or it can be substantially constant. While the funnel 16 can be made from any combination of rigid and/or flexible materials, in an exemplary embodiment the funnel 16 is composed of one or more substantially rigid materials, e.g., medical grade polycarbonate.

Figure 14:
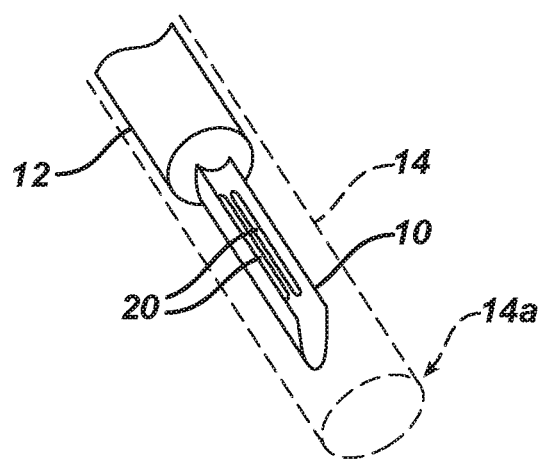
FIG. 14 is a partially transparent perspective view of the scaffold of FIG. 1 attached to the prongs of the delivery shaft and disposed in the cannula in a folded configuration.

In use, the funnel 16 can be attached to the distal end 14a of the cannula 14, and the shaft 12 can be slidably received therein. With the shaft 12 advanced proximal end 12b first into the distal end 16a of the funnel 16 and the distal end 14a of the cannula 14, the prongs 20 can be the last portion of the shaft 12 introduced into the funnel 16 and the cannula 14. Because the prongs 20 can be advanced through the scaffold 10 a predetermined distance from an edge of the scaffold 10, e.g., the length $l_4$, the prongs 20 can be positioned with respect to the scaffold's perimeter to predictably move the scaffold 10 from a planar configuration to a folded configuration as the scaffold 10 moves through the funnel 16 such that the scaffold 10 can be in the folded configuration within the cannula 14. In other words, the tapered passageway 60 of the funnel 16 can guide the scaffold 10 into a folded configuration in which the scaffold 10 is wrapped around the prongs 20, e.g., as illustrated in FIG. 14. A person skilled in the art will appreciate that in a folded configuration, the scaffold 10 can be rolled, as shown, and/or creased. Moreover, because the scaffold 10 can be elliptical and loaded onto the prongs 20 with its tissue side 10b facing down, e.g., away from the shaft's elongate body 18 as illustrated in FIG. 9, and with the prongs 20 at an asymmetrical location along a major axis of the scaffold 10, the scaffold 10 can be folded into a U-shape around the prongs 20 with the tissue side 10b facing the prongs 20. In this way, the tissue side 10b of the scaffold 10 can be better protected within the cannula 14 as the shaft 12 with the scaffold 10 attached thereto slides through the passageway 22 of the cannula 14.

The shaft 12 can be advanced any distance into the cannula 14 to fully contain the scaffold 10 within the cannula's passageway 22. In an exemplary embodiment, the locking mechanism cooperating between the shaft 12 and the cannula 14 can allow the shaft 12 to advance a predetermined distance into the cannula 14 to help ensure that the prongs 20 with the scaffold 10 attached thereto are fully, safely contained within the cannula 14. As discussed above, the locking mechanism can have a variety of configurations, but in this illustrated embodiment, the button 52 in the head 46 of the cannula 14 can engage the groove 24 formed in the shaft 12 to hold the shaft 12 in a locked position within the cannula 14. As the shaft 12 passes through the passageway 22 of the cannula 14, the shaft 12 can move the button 52 from its biased position to the depressed position. Moving the shaft 12 through the passageway 22 in the head 46 can maintain the button 52 in its depressed position, with the shaft 12 passing through an opening formed through the button 52 between the distal and proximal ends 52a, 52b thereof, until the groove 24 reaches the button 52. When the shaft 12 passes an adequate distance through the passageway 22 for the locking feature 24 to reach the button 52 such that the locking feature 24 and the button 52 are aligned, the button 52 can slide into the groove 24, e.g., an inner surface of the locking member 52c can engage the groove 24. The groove 24, having a small diameter than the elongate body 18 in which it is formed, can thus help urge the button 52 from the unlocked to locked position, thereby holding the shaft 12 in a fixed position until the button 52 is pressed at its proximal end 52b and/or the shaft 12 is advanced distally such that its tapered shape can disengage the locking feature 24 from the cannula's locking mechanism. In the locked position, at least the proximal end 12b of the shaft 12 can extend proximally beyond the proximal end 14b of the cannula 14 to allow the shaft 12 to be manipulated from outside the cannula 14 and outside a body of a patient when the cannula 14 is introduced therein. Also in the locked position, the prongs 20 with the scaffold 10 attached thereto can be positioned in a distal portion of the cannula 14 just proximal of the funnel 16. Thus, in the illustrated embodiment, pushing the elongate body 18 distally can unlock the parts without requiring manual pushing of the button 52. The stiffness of the spring 48 and the slope of the taper can determine how much force, which is created to help prevent accidental fall-out of the elongate body 18 from the cannula 14, is required to unlock the parts.

Figure 15:
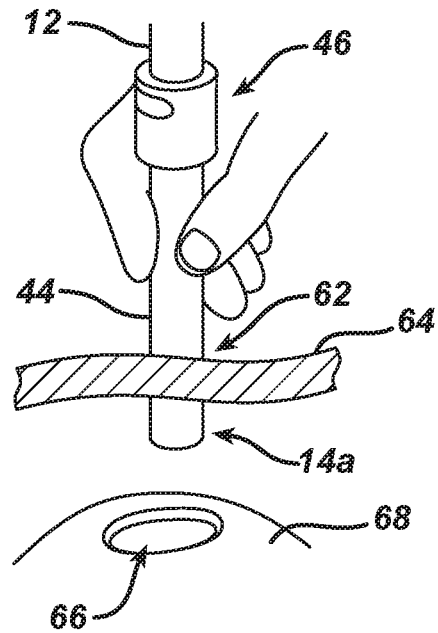
FIG. 15 is a partial cross-sectional perspective view of the cannula of FIG. 1 being advanced through tissue toward a cavity formed at a tissue defect site in a patient.

Once the shaft 12 and the scaffold 10 are back-loaded into the cannula 14, the cannula 14 can be inserted through tissue. A person skilled in the art will appreciate that the scaffold 10, or any other tissue replacement implant, can be introduced into a patient in any way. In one embodiment illustrated in FIG. 15, the cannula 14 can be inserted into a body cavity through a surgically created incision or opening 62 in a tissue 64 to prepare for delivery of the scaffold 10 into the patient. The funnel 16 can be removed from the distal end 14a of the cannula 14 before the cannula 14 is inserted into the patient, which can to help reduce a size of the opening 62. Although the cannula 14 with the shaft 12 disposed therein is shown being initially introduced through the tissue 64, a person skilled in the art will appreciate the cannula 14 can be introduced through the tissue 64 without the shaft 12 disposed in the cannula's passageway 22, such as if the shaft 12 with the scaffold 10 attached thereto is introduced into the cannula 14 through the cannula's proximal end 14b. A person skilled in the art will also appreciate that the cannula 14 can be inserted directly through the tissue 64 as illustrated to help minimize a size of the opening 62, or the cannula 14 can be inserted through an introducer device, e.g., an access port that has a working channel through which another surgical instrument can be advanced.

The distal end 14a of the cannula 14 can help form the opening 62 and/or one or other surgical tools can be used to form the opening 62 through the tissue 64, as will be appreciated by a person skilled in the art. The cannula's elongate body 44 can expand the diameter of the opening 62 to about the diameter D4 of the cannula's elongate body 44 as the elongate body 44 is passed therethrough, thereby helping to minimize the size of the opening 62 and to reduce patient trauma. Because the scaffold 10 can be fully disposed within the cannula 14 in a folded configuration, it can be inserted into the patient through an opening 62 having a diameter that is smaller than a diameter or maximum width of the scaffold 10.

The cannula 14 can be longitudinally advanced any distance through the tissue 64 and positioned in any way relative to the tissue 64. The cannula 14 can also be positioned in any way relative to a cavity 66 formed in tissue, e.g., cartilage 68, at a defect site where the scaffold 10 is to be attached. In an exemplary embodiment, the cannula 14 can be positioned through the tissue 64 such that a longitudinal axis A2 of the cannula 14 (see FIG. 10) and the longitudinal axis A of the shaft 12 are each substantially perpendicular to the cavity 66. Such substantially perpendicular positioning can help more quickly, safely, and accurately position the scaffold 10 from outside the patient's body with respect to the cavity 66.

Figure 16:
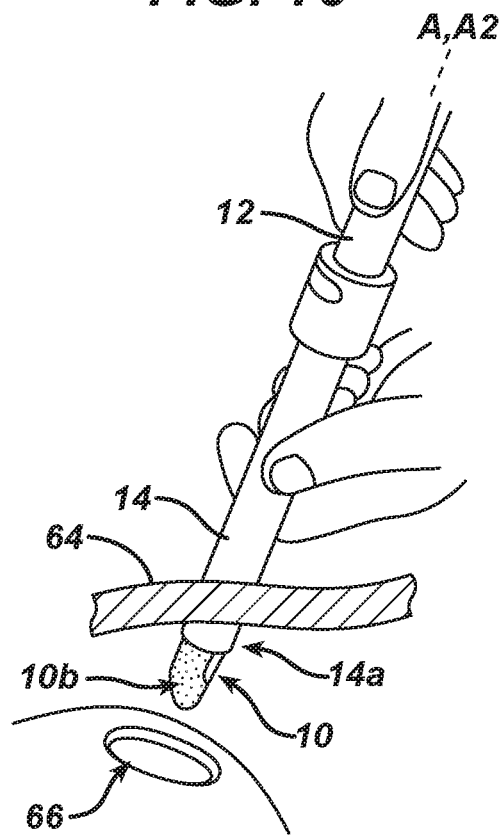
FIG. 16 is a partial cross-sectional perspective view of the delivery shaft of FIG. 1 being distally advanced through the cannula of FIG. 15 showing and the tissue scaffold advancing from the distal end of the cannula.

Once the cannula 14 has been passed through the tissue 64 with, e.g., the cannula's elongate body 44 positioned within the opening 62 and with the cannula's distal end 14a and the head 46 on opposed sides of the tissue 64, the delivery shaft 12 can be distally advanced through the cannula's passageway 22 and out the cannula's distal end 14a and/or the cannula 14 can be proximally retracted to expose the scaffold 10 to deliver the scaffold 10 into the patient. As shown in one embodiment in FIG. 16, the central longitudinal axes A, A2 of the delivery shaft 12 and the cannula 14, respectively, can be aligned substantially perpendicular to a desired location, e.g., above the cavity 66. Although the delivery shaft 12 and the cannula 14 can be located anywhere with respect to the desired location when the scaffold 10 is advanced through and outside the cannula 14, such substantially perpendicular positioning can allow the scaffold 10 to be more accurately delivered to the desired location, which can reduce the amount of movement and positioning of the fragile scaffold 10 inside the body. The shaft 12 can be distally advanced through the passageway 22 in the cannula 14 in any way, such as by holding the shaft 12 in a substantially static position and proximally moving the cannula 14 or such as shown by holding the cannula 14 in a substantially static position and moving the shaft 12 distally therethrough. In the illustrated embodiment the locking mechanism automatically disengages upon distal movement of the shaft 12, but alternatively or in addition, the locking mechanism can be manually disengaged, e.g., by pressing the button 52 on the cannula's head 46, to allow free slidable movement of the shaft 12 within the cannula 14.

Figure 17:
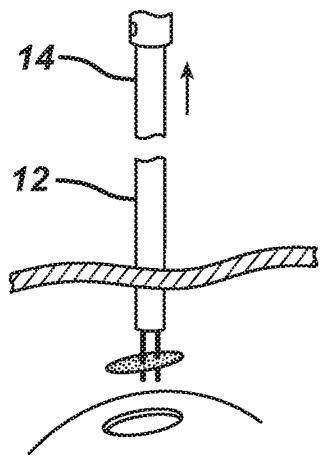
FIG. 17 is a partial cross-sectional perspective view of the cannula of FIG. 16 being removed from around the delivery shaft and from inside the patient.
Figure 18:
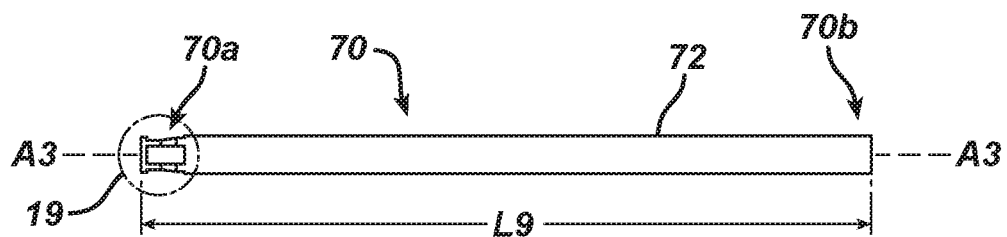
FIG. 18 is a side view of one embodiment of a delivery guide.
Figure 19:
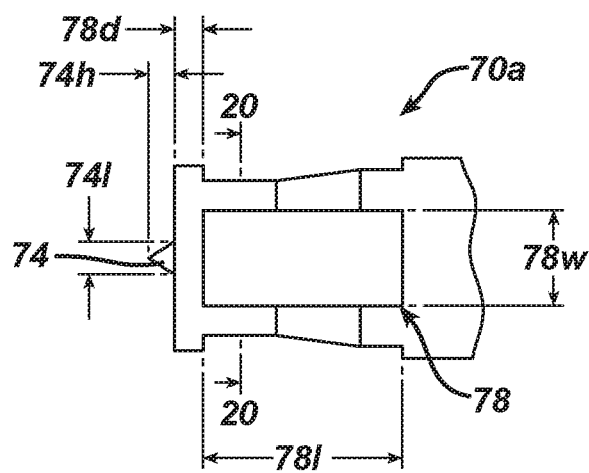
FIG. 19 is an enlarged side view of a distal end of the delivery guide of FIG. 18.
Figure 20:
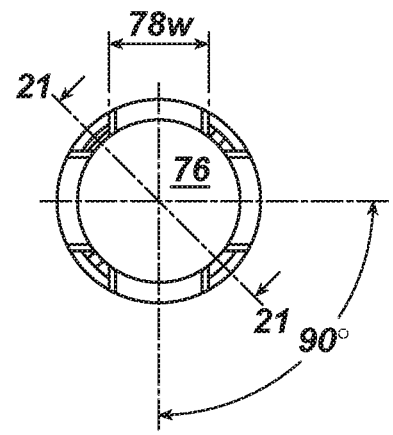
FIG. 20 is a cross-sectional view of the distal end of the delivery guide of FIG. 18.
Figure 21:
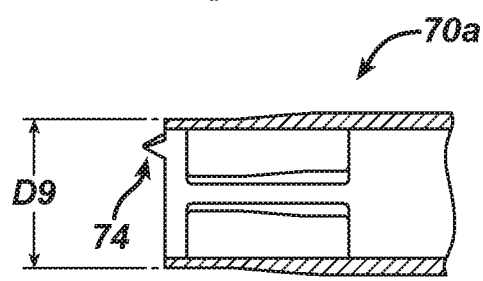
FIG. 21 is a cross-sectional view of the distal end of the delivery guide of FIG. 18.
Figure 22:
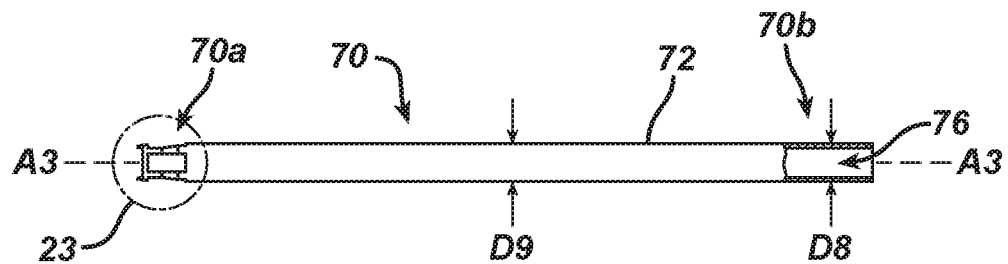
FIG. 22 is another side view of the delivery guide of FIG. 18.

When the scaffold 10 is positioned beyond the distal end 14a of the cannula 14, the scaffold 10 can move from the folded configuration back to the planar configuration. As will be appreciated by a person skilled in the art, the scaffold 10 can gradually move from the folded configuration, shown in FIG. 16, to the planar configuration, shown in FIG. 17, as the scaffold 10 gradually advances distally beyond the cannula's distal end 14a. The scaffold 10 can be formed from a material that causes the scaffold 10 to automatically move to the planar configuration from the folded configuration, but at least one grasper and/or a delivery guide, discussed further below, can optionally be used to grasp and help unfold the scaffold 10.

With the scaffold 10 positioned beyond the distal end 14a of the cannula 14, the scaffold 10 can be detached from the prongs 20 of the shaft 12 and positioned in the cavity 66 for attachment thereto. Positioning of the scaffold 10 in the cavity 66, and/or any other portion of the surgical procedure, can be visualized, e.g., viewed through a lens on a scoping device inserted into the patient and pictured on a visualization screen outside the patient's body. While the scaffold 10 can be removed from the prongs 20 while the shaft 12 is disposed in the cannula 14, in an exemplary embodiment the cannula 14 can be removed from the patient before detaching the scaffold 10 from the delivery shaft 12. As illustrated in one embodiment in FIG. 17, the cannula 14 can be removed from the body of the patient, leaving the scaffold 10 and at least a portion of the shaft 12 inside the patient. The cannula 14 can be removed from the patient in any way, such as by holding the shaft 12 outside the body and moving the cannula 14 proximally as indicated by the directional arrow in FIG. 17. If locking mechanism is not configured to automatically disengage upon proximal movement of the cannula 14 to allow the shaft's locking feature 24 to pass the cannula's locking mechanism, the locking mechanism can be manually disengaged such as by pressing the button 52. Optionally, the prongs 20 can be positioned to abut bone and/or calcified cartilage at a bottom surface of the cavity 66, providing stability to the shaft 12 as the cannula 14 is removed from around the shaft 12.

The scaffold 10 can be removed from the prongs 20 in any way, e.g., holding the scaffold 10 with a grasper and moving the shaft 12 and/or the grasper to remove the scaffold 10 from the prongs 20. Alternatively or in addition, the scaffold 10 can be removed from the prongs 20 using a surgical instrument configured to be advanced over the shaft 12 and configured to help affix the scaffold 10 inside the cavity 66, thereby reducing an amount of instrumentation used during the surgical procedure and improving the accuracy of the scaffold's implantation. Such a surgical instrument can have a variety of configurations, such as one embodiment of a delivery guide 70 illustrated in FIGS. 18-23. Generally, the delivery guide 70 can be configured to remove the scaffold 10 from the prongs 20 of the delivery shaft 12, hold the scaffold 10 in a fixed position at a desired site of implantation, and, without having to be removed from the patient's body, to guide one or more surgical devices configured to help affix the scaffold 10 to the desired site of implantation. The delivery guide 70 can thus help improve efficiency of the surgical procedure, help limit movement of the fragile scaffold 10, and help ensure that the scaffold 10 is affixed within the patient at an intended location.

Figure 26:
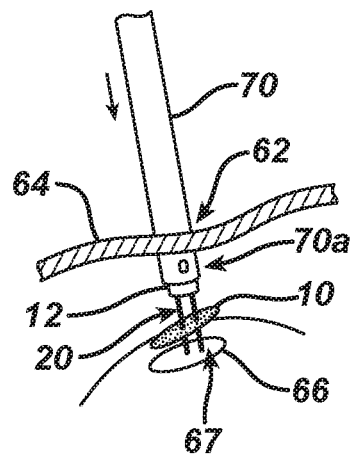
FIG. 26 is a partial cross-sectional perspective view of the delivery guide of FIG. 18 being advanced over the delivery shaft of FIG. 17 and toward the tissue scaffold attached to the delivery shaft.

The delivery guide 70 can have a variety of sizes, shapes, and configurations. As shown in this embodiment, the delivery guide 70 includes an elongate body 72 having an inner lumen or passageway 76 extending between distal and proximal ends 70a, 70b of the guide 70 and having at least one bone-engaging element 74 at the distal end 70a of the delivery guide 70. The delivery guide 70 can have any longitudinal length L9, e.g., about 7.2 in. (182.9 mm). In an exemplary embodiment the delivery guide 70 can be shorter than the delivery shaft 12 to allow the shaft 12 to be disposed in the passageway 76 and proximally extend beyond the guide's proximal end 70b such that the shaft 12 can be more easily manipulated when disposed in the guide 70. The longitudinal length L9 of the guide 70 can also be sufficiently long to allow its distal and proximal ends 70a, 70b to be disposed on opposed sides of a tissue surface when the guide 70 is disposed through the tissue surface, such as shown in FIG. 26 discussed below.

The elongate body 72 can optionally include one or more gripping mechanisms, e.g., finger loops, molded finger depressions, treads, etc., to facilitate holding and manipulation of the guide 70. The guide 70 can alternatively or additionally optionally include a handle at its proximal end 70b and/or other portion of the elongate body 72. The handle can be, for non-limiting example, a substantially cylindrical disc or knob, although as will be appreciated by a person skilled in the art the handle can have any size, shape, and configuration that allows the guide 70 to be held outside the body. A person skilled in the art will appreciate that the guide 70 need not include a handle but instead can be manipulated using, e.g., a proximal portion of the elongate body 72.

Figure 23:
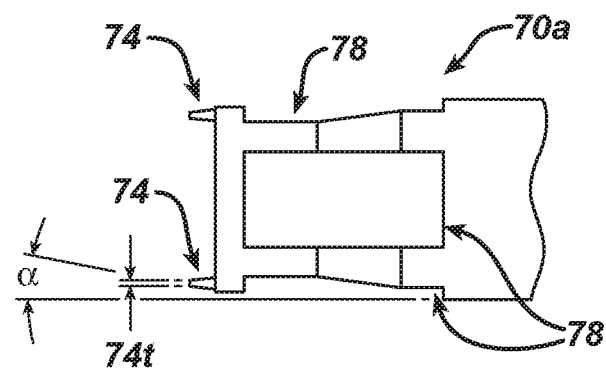
FIG. 23 is an enlarged side view of a distal end of the delivery guide of FIG. 22.

The one or more bone-engaging elements 74 at the guide's distal end 70b can generally be configured to penetrate the scaffold 10, and/or partially penetrate into bone and/or calcified cartilage, to help secure the guide 70, and thus the scaffold 10, against bone and/or calcified cartilage with or without a surgical device present in the guide's passageway 76. The bone-engaging elements 74 can have any configuration. In the illustrated embodiment the guide 70 includes four bone-engaging elements 74, but the guide 70 can include any number of bone-engaging elements 74, e.g., two. Moreover, each of the bone-engaging elements 74 can be the same or different from any other of the bone-engaging elements 74. The bone-engaging elements 74 can be configured as teeth or prongs as shown, with or without tapered distal tips configured to help the bone-engaging elements 74 engage bone and/or calcified cartilage. The bone-engaging elements 74 are illustrated as isosceles triangles having a height 74h of about 0.06 in. (1.5 mm), a length 74l of about 0.03 in. (0.75 mm), and a thickness of about 0.01 in. (0.25 mm), but the bone-engaging elements 74 can have any size and shape. The bone-engaging elements 74 can be arranged at the guide's distal end 70a in any configuration, such as equidistantly spaced radially around a central longitudinal axis A3 of the guide 70 along the guide's perimeter, as illustrated in FIG. 23. The bone-engaging elements 74 can extend substantially parallel to the guide's longitudinal axis A3 or, as illustrated, the bone-engaging elements 74 can angle radially inwards at an angle α to help better grip bone and/or calcified cartilage. In some embodiments including a plurality of the bone-engaging elements 74, the bone-engaging elements 74 can cover a distal end surface of the elongate body 72 such that the bone-engaging elements 74, e.g., a plurality of teeth, can form a textured bone-engaging surface.

Although the bone-engaging elements 74 are shown integrally formed with the elongate body 72, any one or more of the bone-engaging elements 74 can be movably coupled to the elongate body 72. For non-limiting example, the bone-engaging elements 74 can be retractable such that in an extended position the bone-engaging elements 74 can extend distally beyond the guide's distal end 70a and in a retracted position can be contained within the elongate body 72. Retraction and extension of movable bone-engaging elements can be controlled in any way, as will be appreciate by a person skilled in the art, such as through actuation of a control mechanism, e.g., a knob, a button, a lever, an electronic signal communicator, etc., at the proximal end 70b of the guide 70. In some embodiments, the bone-engaging elements 74 can be removably coupled to the guide 70.

As mentioned above, the guide 70 can be configured to be removably coupled to the shaft 12 with the shaft's elongate body 18 slidably receivable within the inner passageway 76 of the guide 70. The guide's passageway 76 can thus, as shown in this embodiment, be substantially cylindrical-shaped to match the shape of the shaft 12. The corresponding cylindrical shapes of the guide's passageway 76 and the shaft's elongate body 18 can allow the shaft 12 to be both linearly and rotatably movable within the inner passageway 76, which can help position the guide 70 relative to the shaft 12 and to the scaffold 10 attached to the prongs 20 of the shaft 12. The diameter D1 of the shaft's elongate body 18 can thus be less than a diameter D8 of the guide's passageway 76 to allow the elongate body 18 to be movable therein. The diameter D8 can have any size, e.g., about 0.305 in. (7.7 mm). The elongate body 72 can also have any shape, e.g., cylindrical, etc., and have any diameter D9, e.g., about 0.375 in. (9.5 mm). The elongate body's diameter D9 can be constant along the longitudinal length L9 of the guide 70, or the diameter D9 can vary with, e.g., the elongate body 72 having a different diameter D9 in at least a portion of the distal end 70a.

The elongate body 72 can also include one or more windows or cut-outs 78 adjacent the distal end 70a. One or more windows at the guide's distal end 70a are optional, and they can be configured to enable viewing of at least one surgical instrument and/or a surgical site within the guide's passageway 76 at least at the distal end 70a. The cut-outs 78 can have any configuration. As illustrated in this embodiment, the cut-outs 78 can include one or more holes or openings formed in a sidewall of the elongate body 72 of the guide 70 such that the cut-outs 78 are in communication with the guide's passageway 76. Although four cut-outs 78 are shown, the guide 70 can include any number of cut-outs 78. Moreover, each of the cut-outs 78 can be the same or different from any other of the cut-outs 78. The cut-outs 78 are illustrated as rectangular shapes having a length 78*l* of about 0.375 in. (9.5 mm) and a width 78*w*, e.g., about 0.18 in. (4.8 mm), but the cut-outs 78 can have any size and shape. The cut-outs 78 can be arranged at the guide's distal end 70a in any configuration, such as equidistantly spaced radially around a central longitudinal axis A3 of the guide 70, e.g., about 90° apart as illustrated. The windows 78 can be located any longitudinal distance 78d from a distal-most end of the guide 70, e.g., about 0.05 in. (1.3 mm), to allow for viewing of components within the passageway 76 in the distal end 70a of the guide 70.

Figure 24:
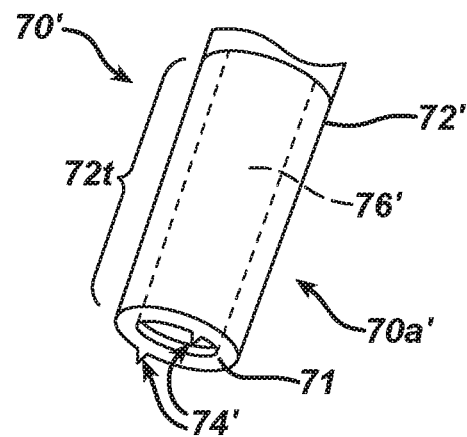
FIG. 24 is a perspective view of a distal end of another embodiment of a delivery guide having a transparent distal portion and having a removable distal ring with at least one bone-engaging element extending therefrom.

In an alternate embodiment of a delivery guide 70', illustrated in FIG. 24, the guide 70' can be configured similar to the guide 70 except that a window formed adjacent a distal end 70a' can be in the form of a transparent portion 72t of an elongate body 72' of the guide 70'. The transparent portion 72t can be configured to allow visualization through the guide 70' while helping to keep tissue, fluid, and any other material from passing into an inner lumen 76' of the guide 70' through a side of the elongate body 72'. Although the transparent portion 72t is illustrated only at a distal end of the elongate body 72', the transparent portion 72t can extend along any full or partial length of the elongate body 72'. The distal transparent portion 72t can be a continuous transparent portion, e.g., a transparent cylindrical body as shown, although as will be appreciated by a person skilled in the art, the distal transparent portion can includes a plurality of transparent windows formed in and arranged around the elongate body 72' similar to the cut-outs 78. A person skilled in the art will also appreciate that the term "transparent" as used herein is intended to include any combination of one or more see-through materials including optically clear material and translucent material.

As mentioned above, instead of bone-engaging elements being integrally formed with a delivery guide, the bone-engaging elements can be removably coupled to the guide. The alternate guide 70' illustrates one embodiment of one or more bone-engaging elements 74' extending distally from a distal ring 71 that is configured to be removably coupled to the guide's distal end 70a' in any way appreciated by a person skilled in the art, e.g., threadably attached, snap fit, etc. In this way, distal rings having different sizes and shapes and/or having different numbers, sizes, shapes, etc. of bone-engaging elements can be coupled to a delivery guide to allow the delivery guide to better accommodate differently sized and shaped tissue defect sites and differently sized and shaped tissue scaffolds. Modular distal rings can optionally be supplied with a delivery guide as part of a kit.

Figure 25:
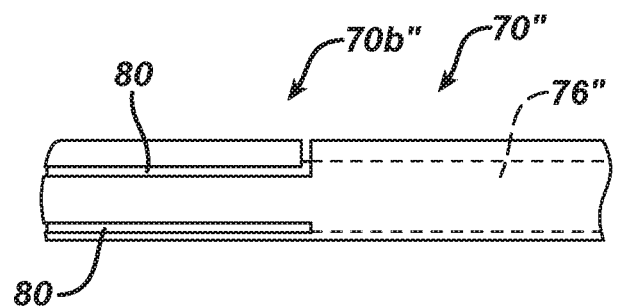
FIG. 25 is a perspective view of a proximal end of another embodiment of a delivery guide having an alignment mechanism.

In another alternate embodiment of a delivery guide 70", illustrated in FIG. 25, the guide 70" can be configured similar to the guide 70 or the guide 70' except that the guide 70" can include at least one alignment mechanism configured to position a tool, e.g., a delivery shaft, a punch tool, a fastener-applying tool, etc., inserted through an inner lumen or passageway 76" extending between a distal end (not shown) and a proximal end 70b" of the guide 70" in a predetermined radial position relative to the guide 70". In this way, a position of the tool at the surgical site can be known even if it is difficult or impossible to view the tool at the surgical site, such as can often be the case in a mini-open surgical procedure. The optional alignment mechanism can have a variety of sizes, shapes, and configurations. For non-limiting example, the alignment mechanism can include an alignment guide label printed, embossed, or otherwise viewable on the guide 70" that indicates a proper radial positioning of a surgical tool inserted into the passageway 76". The surgical tool can have a corresponding alignment guide label such that matching alignment guide labels can be aligned to help ensure proper positioning of the tool within the guide 70". In the illustrated embodiment, the alignment mechanism includes at least one elongate slot 80 formed in at least the proximal end 70b" of the guide 70". A surgical tool inserted through the proximal end 70b" of the guide 70" can have one or more corresponding alignment mechanisms, e.g., pins, protrusions, elongate tracks, etc., configured to be received in and slide through the slots 80 to orient the tool in a particular radial position such that its position at the distal end of the guide 70" can be known even without visual confirmation.

Figure 27:
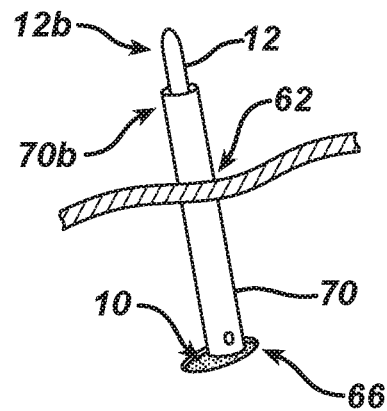
FIG. 27 is a partial cross-sectional perspective view of the delivery guide of FIG. 26 advanced over the delivery shaft and holding the tissue scaffold in a fixed position in a cavity at the tissue defect site.
Figure 28:
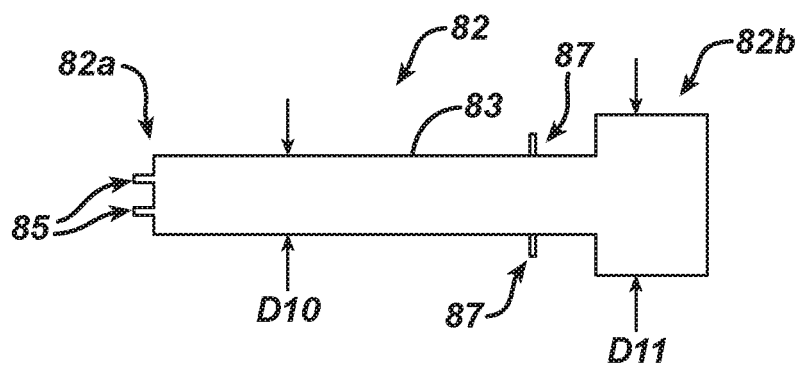
FIG. 28 is a side view of one embodiment of a punch tool.

Regardless of the type of delivery guide introduced into a body of a patient to help remove the scaffold 10 from the prongs 20 of the delivery shaft 12, the delivery guide can be introduced into the patient's body over the shaft 12. In one embodiment illustrated in FIGS. 26 and 27, with the shaft 12 disposed through the opening 62 in the tissue 64, the delivery guide 70 can be advanced distal end 70a first over the shaft 12 such that the shaft 12 can be slidably received in the guide's passageway 76. At any time prior to contact of the guide's distal end 70a with the scaffold 10 attached to the prongs 20, the scaffold 10 can be positioned above and aligned with the cavity 66, as illustrated in FIG. 26, such that distally advancing the scaffold 10 can position the scaffold 10 within the cavity 66, as shown in FIG. 27. The prongs 20 can be positioned to contact at least a surface of a bone 67 at a bottom surface of the cavity 66, thereby positioning the scaffold 10 with respect to the cavity 66 and providing stability to the shaft 12 as the guide 70 is advanced over the elongate body 18 of the shaft 12. As mentioned above, the prongs 20 can be distally tapered, which can help the prongs 12 grip and/or penetrate the bone 67. Additionally, the bone 67 can additionally or alternatively include calcified cartilage.

The delivery guide 70 can be distally advanced over the shaft 12, as shown by the directional arrow in FIG. 26, with the guide's distal end 70a eventually contacting the scaffold 10 on the prongs 20. Because the guide 70 can be configured to surround the shaft 12, the distal end 70a of the guide 70 can distally advance over shaft 12 and hence over the prongs 20 extending therefrom and contact the scaffold 10 without contacting the prongs 20. The delivery guide 70 can be distally advanced through the tissue 64 until the distal end 70a of the guide 70 pushes the scaffold 10 toward and into the cavity 66, which can optionally also move the scaffold 10 from the folded configuration to the planar configuration. The bone-penetrating elements 74 can penetrate through the scaffold 10 and contact at least a surface of the bone 67, which can help hold the delivery guide 70 in position in the patient and temporarily hold the scaffold 10 in a fixed position in the cavity 66. A person skilled in the art will appreciate that one or more of the bone-penetrating elements 74 can be configured to not penetrate through the scaffold 10 and hence not contact the bone 67. With the guide 70 holding the scaffold 10 in a desirable position in the cavity 66, the shaft 12 can be removed from the guide 70 and from the patient's body. The shaft 12 can be removed in any way, such as manipulating the proximal end 12b of the shaft 12 proximally extending beyond the guide's proximal end 70b, as shown in FIG. 27, and proximally pulling the shaft 12. Movement of the guide 70 against the scaffold 10 can push the scaffold 10 off one or more of the prongs 20, but if any of the prongs 20 extend through the scaffold 10 after the guide 70 holds the scaffold 10 in the cavity 66, proximal movement of the shaft 12 through the guide's passageway 76 can pull the prongs 20 out of the scaffold 10.

Optionally, with the scaffold 10 in an implantation position within the cavity 66, the scaffold 10 can be attached to the patient. A person skilled in the art will appreciate that the scaffold 10 in the implantation position can fit entirely within the cavity 66 or that a portion of the scaffold 10 can extend outside the cavity 66 if, e.g., the scaffold 10 was cut to a size larger than the cavity 66. The scaffold 10 can be attached to the patient in any way, as will be appreciated by a person skilled in the art. In some embodiments, the guide 70 can be removed from the patient after the guide 70 advances the scaffold 10 into the implantation position, but in an exemplary embodiment, the guide 70 remains in place while at least one surgical tool is advanced through the guide's passageway 76 to affix the scaffold 10 to the patient.

Any one or more surgical tools can be used to affix the scaffold 10 in any way. In one embodiment, illustrated in FIGS. 28-31, a bone preparation tool such as a punch tool 82 can be used to punch at least one hole or opening 86 in the scaffold 10 and in the bone 87 underlying the scaffold 10, and a scaffold seating tool such as a fastener-applying tool 88 can be used to apply at least one securing mechanism or fastener 90 through the one or more openings 86 created by the punch tool 82 to fasten the scaffold to the bone 87. In some embodiments, a single tool can be configured as a bone preparation tool and a scaffold seating tool, e.g., a staple inserter device such as those discussed in more detail in previously mentioned U.S. Pat. No. 6,447,517 issued Sep. 10, 2002 titled "Instrument For Inserting Graft Fixation Device," U.S. Pat. No. 6,179,840 issued Jan. 30, 2001 titled "Graft Fixation Device And Method," and U.S. Pat. No. 6,423,073 issued Jul. 23, 2002 titled, "Instrument For Inserting Graft Fixation Device." The punch tool 82 and the fastener-applying tool 88 can each be separately advanced through the delivery guide 70 holding the scaffold 10 in the cavity 66, thereby allowing the punch tool 82 and the fastener-applying tool 88 to be more accurately positioned relative to the scaffold 10 and help assure that the one or more fasteners 90 applied by the fastener-applying tool 88 are positioned at a desirable location with respect to the scaffold 10 and that the one or more fasteners 90 properly align with the formed one or more openings 86. A person skilled in the art will appreciate that other bone preparation tools and scaffold seating tools can be used, if one or either is used at all in applying the scaffold 10. For non-limiting example, a fastener can come from the bone 87 and then through the scaffold 10.

The punch tool 82 can have a variety of sizes, shapes, and configurations. Generally, the punch tool 82 can include any punch tool configured to create one or more openings or holes in a tissue scaffold and in bone, as will be appreciated by a person skilled in the art. Non-limiting embodiments of punch tools can be found in U.S. Pat. No. 6,447,517 issued Sep. 10, 2002 titled "Instrument For Inserting Graft Fixation Device," U.S. Pat. No. 6,179,840 issued Jan. 30, 2001 titled "Graft Fixation Device And Method," and U.S. Pat. No. 6,423,073 issued Jul. 23, 2002 titled, "Instrument For Inserting Graft Fixation Device," which are hereby incorporated by reference in their entireties. In one embodiment illustrated in FIG. 28, the punch tool 82 can include an elongate body 83 having at least one bone-penetrating element 85 at a distal end 82a of the punch tool 82. The punch tool 82 can have any longitudinal length, but in an exemplary embodiment the punch tool 82 can be longer than the delivery guide 70 to allow the punch tool 82 to be disposed in the passageway 16 and proximally extend beyond the guide's proximal end 70b when distal ends 70a, 82a of the guide 70 and the punch tool 82 are each contacting the scaffold 10 inside the patient. The bone-penetrating elements 85 can have any size, shape, and configuration. The bone-penetrating elements 85 can generally be configured as teeth or prongs, similar to the bone-engaging elements 74 discussed above, that are configured to at least partially penetrate into bone to help form a hole or opening in bone. The bone-penetrating elements 85 of the punch tool 82 can be different, e.g., sharper and/or longer, than the bone-engaging elements 74 of the guide 70 to allow the bone-penetrating elements 85 of the punch tool 82 to form appropriate holes in bone to receive fasteners. As illustrated, the bone-penetrating elements 85 of the punch tool 82 can be cylindrical, rigid, solid members.

As mentioned above, the punch tool 82 can be configured to be removably coupled to the guide 70 with the punch tool's elongate body 83 slidably received within the inner passageway 76 of the guide 70. The punch tool's elongate body 83 can thus, as shown in this embodiment, be substantially cylindrical-shaped to match the shape of the inner passageway 76. The corresponding cylindrical shapes of the guide's passageway 76 and the punch tool's elongate body 83 can allow the punch tool 82 to be both linearly and rotatably movable within the inner passageway 76, unless an alignment mechanism, e.g., one or more pins 87, is present to prevent rotational motion of the punch tool 82 within the passageway 76 of the guide 70. The punch tool's elongate body 83 can thus have a diameter D10 less than the diameter D8 of the guide's inner passageway 76 to allow the elongate body 83 to be movable therein. Conversely, the punch tool's proximal end 82b can have a diameter D11 that is greater than the diameter D8 of the guide's passageway 76 and greater than the elongate body's diameter D10. In this way, the punch tool's proximal end 82b can serve as a stop mechanism configured to limit a distance that the punch tool 82 extends into the guide 70 and thus into bone.

Although the punch tool 82 can be a solid member as shown, the punch tool 82 can include one or more passageways formed therethrough. For non-limiting example, the punch tool 82 can include a tunnel extending through its distal and proximal ends 82a, 82b that is configured to receive at least one surgical instrument disposed therethrough, e.g., a vacuum device configured to suction fluid, tissue, etc. away from a surgical site.

Figure 29:
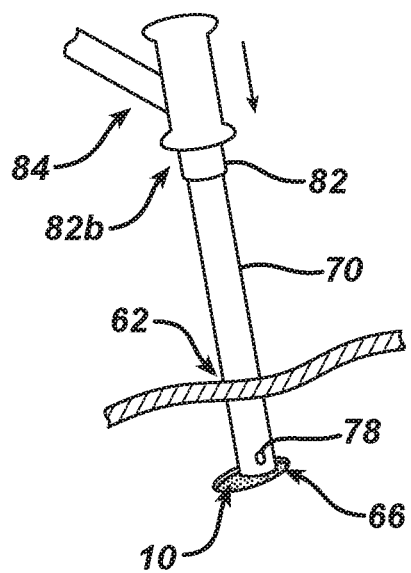
FIG. 29 is a partial cross-sectional perspective view of the punch tool of FIG. 28 disposed in the delivery guide of FIG. 27, with the delivery shaft removed from the delivery guide, and a hammer hitting a proximal end of the punch tool to punch one or more holes in the tissue scaffold in the cavity and in bone underlying the tissue scaffold.

In use, as illustrated in FIG. 29, the punch tool 82 can be distally advanced into the delivery guide 70 and through the opening 62 in the tissue 64 until a distal end (not shown) of the punch tool 82 contacts the scaffold 10 or is otherwise desirably positioned with respect to the scaffold. Proper positioning of the punch tool 82 inside the guide 70 can be verified by feel and/or by visualization through the cut-outs 78 in the guide 70. If the punch tool 82 and the guide 70 include an alignment mechanism, the alignment mechanism can align the punch tool 82 with respect to the guide 70 before and/or after the punch tool is advanced therethrough to predictably align the punch tool's distal end with respect to the scaffold 10 and thus also predictably position the openings 86 formed by the punch tool 82. The alignment mechanism can also align the bone-penetrating elements 85 of the punch tool 82 at a predetermined radial position relative to the guide 70. Generally, with the punch tool 82 disposed in the guide's passageway 76, the punch tool 82 can be distally advanced, e.g., by hitting the proximal end 82b of the punch tool 82 with a hammer 84 one or more times, to create the one or more openings 86 in the scaffold 10 and in the bone 87 underlying the scaffold 10. The punch tool 82 is optionally used, but because the bone 87 can be very hard, forming one or more openings 86 through the scaffold 10 and into the bone 87 can ease application of the one or more fasteners 90. Any time after the punch tool 82 has formed the openings 86 as desired, the punch tool 82 can be removed from the patient, e.g., by proximally moving the punch tool 82 through and out of the guide 70. Distal pressure can be applied to the guide 70 as the punch tool 82 is removed, thereby holding the scaffold 10 in place.

Figure 30:
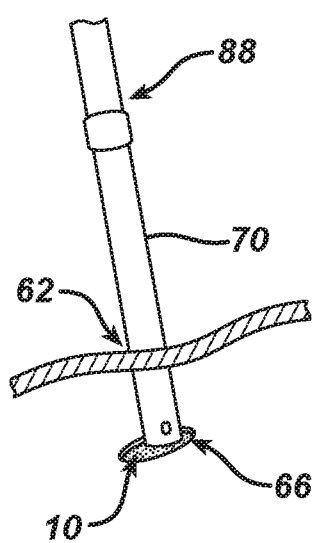
FIG. 30 is a partial cross-sectional perspective view of a fastener-applying tool disposed in the delivery guide of FIG. 29, with the punch tool removed from the delivery guide, and applying one or more fasteners through the holes formed by the punch tool.

As shown in one embodiment in FIG. 30, after the punch tool 82 is removed from the guide 70, the fastener-applying tool 88 can be distally advanced into the delivery guide 70 and through the opening 62 in the tissue 64 similar to the punch tool 82. Proper positioning of the fastener-applying tool 88 inside the guide 70 can also be similarly verified by feel and/or by visualization through the cut-outs 78 in the guide 70. If present, an alignment mechanism can also be similarly used to align the fastener-applying tool 88 with respect to the guide 70 and the scaffold 10. The punch tool 82 and the fastener-applying tool 88 can be similarly configured with alignment mechanisms such that the punch tool 82 and the fastener-applying tool 88 are similarly radially oriented within the guide 70 at predetermined positions such that legs of a fastener 90 applied by the fastener-applying tool 88 can extend into holes 86 created by the punch tool 82. The alignment mechanism can thus help ensure that the fastener-applying tool 88 is positioned to apply the one or more fasteners 90 through the holes 86 formed by the punch tool 82, e.g., without requiring the position of the fastener-applying tool 88 in the patient to be visually or otherwise verified. The fastener-applying tool 88 can be actuated to apply one or more fasteners in any way. The fastener-applying tool 88 can include any fastener-applying tool configured to apply one or more fasteners to a tissue scaffold, as will be appreciated by a person skilled in the art. Generally, the fastener-applying tool 88 can have at last one fastener-retaining member on a distal end of the fastener-applying tool 88 and be configured to retain at least one fastener with the fastener-retaining member and to apply at least one fastener through the scaffold 10 to the bone 87 underlying the scaffold 10. Non-limiting embodiments of fastener-applying tools can be found in previously mentioned U.S. Pat. No. 6,447,517 issued Sep. 10, 2002 titled "Instrument For Inserting Graft Fixation Device," U.S. Pat. No. 6,179,840 issued Jan. 30, 2001 titled "Graft Fixation Device And Method," and U.S. Pat. No. 6,423,073 issued Jul. 23, 2002 titled, "Instrument For Inserting Graft Fixation Device." After one or more fasteners 90 are applied to attach the scaffold 10 to the bone 87, the fastener-applying tool 88 and the guide 70 can be removed from the body of the patient, e.g., by proximally moving the fastener-applying tool 88 and the guide 70 together or separately through and out of the opening 62 in the tissue 64.

Figure 31:
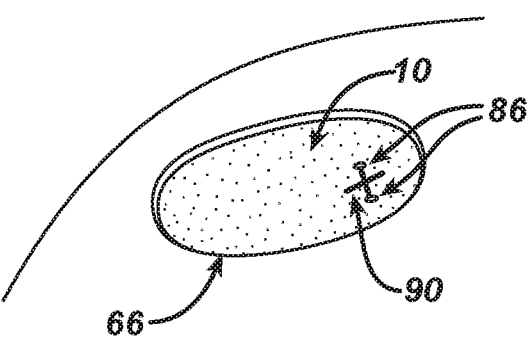
FIG. 31 is a perspective view of the tissue scaffold of FIG. 30 attached to patient with a fastener.

Although only one X-shaped fastener 90 is shown in FIG. 31 attaching the scaffold 10 to the patient, any number of fasteners 90 can be used to affix the scaffold 10 within the cavity 66. A person skilled in the art will appreciate that although the fasteners 90 are illustrated as staples, the one or more fasteners used to attach the scaffold 10 to the patient can include one or more types of fasteners, e.g., a staple, tissue tack, suture, adhesive, etc., in any combination. The delivery guide 70 can be repositioned one or more times with respect to the scaffold 10 to facilitate punching one or more additional holes in the scaffold 10 using a punch tool advanced through the guide 70 and to facilitate application of one or more additional fasteners through the one or more additional holes using a fastener-applying tool advanced through the guide 70.

The devices discussed herein can be made from any combination of rigid and/or flexible materials, but in an exemplary embodiment the materials are biocompatible. A person skilled in the art will appreciate that the terms "flexible" and "rigid" as used herein are intended to encompass a variety of configurations. Generally, a "flexible" member has some degree of elasticity, e.g., is capable of bending without breaking, while a "rigid" member lacks elasticity. In an exemplary embodiment, the devices or at least portions thereof are composed of at least one biocompatible material, e.g., plastic, titanium, stainless steel, etc.

A person skilled in the art will appreciate that the present invention has application in conventional endoscopic and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for delivering a tissue scaffold, comprising:
    advancing a first surgical tool having a tissue scaffold releasably coupled to a distal end thereof into a body of a patient to align the tissue scaffold with a cavity at a defect site,
    then advancing a second surgical tool over the first surgical tool such that the first surgical tool is within a passageway of the second surgical tool and such that a distal end of the second surgical tool comes into contact with the tissue scaffold and holds the tissue scaffold within the cavity, and
    removing the first surgical tool from the passageway of the second surgical tool such that the tissue scaffold remains held in the cavity by the second surgical tool.

2. The method of claim 1, wherein the tissue scaffold is releasably coupled to the first surgical tool by at least one prong extending distally from the first surgical tool and piercing the tissue scaffold.

3. The method of claim 2, wherein the advancement of the second surgical tool over the first surgical tool causes the tissue scaffold to be released from the at least one prong.

4. The method of claim 2, wherein the removal of the first surgical tool from the passageway of the second surgical tool causes the tissue scaffold to be released from the at least one prong.

5. The method of claim 1, wherein the second surgical tool is advanced over the first surgical tool until a bone-engaging element at the distal end of the second surgical tool contacts bone defining a surface of the cavity.

6. The method of claim 1, further comprising, after the removal of the first surgical tool, advancing a third surgical tool into the second surgical tool to fasten the tissue scaffold within the cavity.

7. The method of claim 1, wherein advancing the first surgical tool includes the distal end of the first surgical tool being advanced through a cannula with the tissue scaffold in a folded configuration, and the tissue scaffold automatically moves from the folded configuration to an unfolded configuration when the distal end of the first surgical tool exits the cannula.

8. A tissue scaffold delivery system, comprising:
    a first surgical tool having an elongate body and having a prong extending distally from the elongate body; and
    a second surgical tool having an elongate body and having a passageway within the elongate body, the passageway being configured to slidably receive the first surgical tool therein with a tissue scaffold releasably coupled to the prong such that a tooth extending distally from the elongate body of the second surgical tool pushes against the tissue scaffold and the tissue scaffold is released from the prong in response to a distal end of the second surgical tool moving distally beyond a distal end of the elongate body of the first surgical tool.

9. The system of claim 8, wherein the second surgical tool has a window in a distal portion of the elongate body thereof, the window being configured to provide visualization therethrough of the first surgical tool within the passageway of the second surgical tool.

10. The system of claim 8, wherein the second surgical tool is configured to hold the tissue scaffold against bone after the tissue scaffold has been released from the prong; and
    further comprising a third surgical tool having an elongate body and being configured to be slidably received in the passageway of the second surgical tool and fasten the tissue scaffold to bone with the second surgical tool holding the tissue scaffold against bone.

11. A tissue scaffold loading system, comprising:
    a tissue scaffold loading device having a body and a guide member extending above the body, the body having a surface with at least one opening formed therein, the surface being configured to receive a tissue scaffold thereon that covers the at least one opening, the guide member having at least one channel formed therein, and the at least one channel being configured to slidably receive a surgical tool therein such that the surgical tool pierces through a tissue scaffold on the surface at a predetermined location of the tissue scaffold and then the surgical tool enters the at least one opening.

12. The system of claim 11, wherein the guide member has a surface that faces the surface of the body, the surface of the guide member being configured to abut a perimeter of a tissue scaffold on the surface of the body and thereby position the tissue scaffold over the at least one opening and under the at least one channel.

13. The system of claim 11, wherein the at least one channel has a longitudinal axis that is substantially perpendicular to the surface of the body.

14. The system of claim 11, wherein the guide member has a first arm extending substantially perpendicular from the body, the guide member has a second arm extending substantially perpendicular from the first arm, and the at least one channel is formed in the second arm.

15. The system of claim 14, wherein the second arm extends over the surface of the body and is substantially parallel to the surface of the body.

16. The system of claim 14, wherein a length of the second arm defines the predetermined location.

17. The system of claim 11, further comprising a surgical tool including an elongate body having at least one prong extending distally therefrom, the at least one prong being configured to slide distally within the at least one channel, pierce through a tissue scaffold on the surface, and enter the at least one opening.

18. The system of claim 17, wherein the at least one prong having the tissue scaffold pierced thereby is configured to slide within the at least one opening in a direction away from the guide member.

19. The system of claim 17, wherein the guide member has a first arm extending substantially perpendicular from the body, the guide member has a second arm extending substantially perpendicular from the first arm, and a length of the second arm defines a predetermined distance from a perimeter of a tissue scaffold on the surface that the at least one prong can pierce through the tissue scaffold on the surface.

* * * * *